(12) United States Patent
Gil et al.

(10) Patent No.: US 7,977,335 B2
(45) Date of Patent: Jul. 12, 2011

(54) METHODS OF PREVENTING AND REDUCING THE SEVERITY OF STRESS-ASSOCIATED CONDITIONS

(75) Inventors: Daniel W. Gil, Corona Del Mar, CA (US); Scott Whitcup, Laguna Hills, CA (US); Mitchell F. Brin, Newport Beach, CA (US); John E. Donello, Dana Point, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/114,727

(22) Filed: May 2, 2008

(65) Prior Publication Data
US 2008/0207628 A1 Aug. 28, 2008

Related U.S. Application Data

(63) Continuation of application No. 10/607,439, filed on Jun. 25, 2003, now abandoned.

(51) Int. Cl.
*A61K 31/198* (2006.01)
(52) U.S. Cl. ...................................... 514/249
(58) Field of Classification Search .................. 514/259, 514/396, 249
See application file for complete search history.

(56) References Cited

U.S. PATENT DOCUMENTS

| | | | |
|---|---|---|---|
| 5,795,909 A | 8/1998 | Shashoua et al. | |
| 6,444,681 B1 | 9/2002 | Flavahan et al. | |
| 6,576,636 B2 | 6/2003 | Webb et al. | |
| 6,602,902 B2 | 8/2003 | Shashoua et al. | |
| 7,160,890 B2 | 1/2007 | Castelhano et al. | |
| 2003/0059471 A1 | 3/2003 | Compton et al. | |
| 2003/0073708 A1 | 4/2003 | Castelhano et al. | |
| 2004/0242588 A1 | 12/2004 | Dejovin et al. | |
| 2005/0276830 A1 | 12/2005 | Dejovin et al. | |
| 2006/0171974 A1 | 8/2006 | Dejovin et al. | |
| 2006/0264515 A1 | 11/2006 | Dejovin et al. | |

FOREIGN PATENT DOCUMENTS

| | | |
|---|---|---|
| IN | 188750 | 11/2002 |
| WO | WO96-25163 | 8/1996 |
| WO | WO99-30690 | 6/1999 |
| WO | WO00-24375 | 5/2000 |
| WO | WO00-76502 | 12/2000 |
| WO | WO00-76520 | 12/2000 |
| WO | WO03-048120 | 6/2003 |
| WO | WO2005-010025 | 2/2005 |
| WO | WO2005-115395 | 12/2005 |

OTHER PUBLICATIONS

Watts et al. Delayed hypersensitivity to brimonidine tartrate 0.2% associated with high intraocular pressure. Eye, Mar. 2002, vol. 16, No. 2 pp. 132-135, abstract.*

Flavahan et al, "Increased alpha2-Adrenergic Constriction of Isolated Arterioles in Diffuse Scleroderma", Arthritis & Rheumatism, vol. 43, No. 8, pp. 1886-1890, Aug. 2000.
Flavahan et al, "Sympathetic Purinergic Vasoconstriction and Thermosensitivity in a Canine Cutaneous Vein", J. Pharmacol. Exp. Ther. 239, No. 3, 784-89, 1986.
Flavahan et al, "Cooling and Alpha-1- and Alpha2-Adrenergic Responses in Cutaneous Veins: Role of Receptor Reserve", Am. J. Physiol. No. 5, H950-H955, 1985.
Vanhoutte et al, "Modulation of Postjunctional Alpha-Adrenergic Responsiveness by Local Changes in Temperature", Clin. Sci., 68 (Suppl 10), 121S-23S, 1985.
Pollock et al, "Control of arteriovenous anastomoses in rabbit ear model of digital perfusion", The American Journal of Physiology, vol. 271, No. 5, pp. H-2007-13, 1996.
Chotani et al, "Silent alpha (2C)-adrenergic receptors enable cold-induced vasoconstriction in cutaneous arteries", American Journal of Physiology-Heart and Circulatory Physiology, vol. 278, No. 4, 47-4, pp. H1075-H1083, 2000.
Fuchs et al, "Heat, but not mechanical hyperalgesia, following adrenergic injections in normal human skin", Pain: 90(1-2), 15-23, 2001.
Clouse et al, "Short-term treatment with transdermal nicotine affects the function of canine saphenous veins", Vascular medicine, vol. 5, No. 2, pp. 75-82, 2000.
Sodhi et al, "Dermatological side effects of brimonidine: A report of three cases", Journal of Dermatology, vol. 30, No. 9, pp. 697-700, 2003.
Watts et al, "Delayed hypersensitivity to brimonidine tartrate 0.2 % associated with high intraocular pressure", Eye, vol. 16, No. 2, pp. 132-135, 2002.
Blondeau et al, "Allergic reactions to brimonidine in patients treated for glaucoma", Canadian Journal of Opthalmology, vol. 37, No. 1, pp. 21-26, 2002.
Supplemental Response to Sep. 20, 2007 Office Action and Sustance of the Intervies Under 37 CFR 1.133(b)-SN U.S. Appl. No. 10/853,586.
Declaration Under 37 CFR 1.132 in U.S. Appl. No. 10/853,585, Jan. 8, 2008.
Office Communication Date Mailed Sep. 20, 2007 in U.S. Appl. No. 10/853,585.
Response to Final Office Action Dated Sep. 20, 2007 in U.S. Appl. No. 10/853,585.

* cited by examiner

*Primary Examiner* — Jennifer M Kim
(74) *Attorney, Agent, or Firm* — Joel B. German; Debra D. Condino; Allergan, Inc.

(57) ABSTRACT

The present invention provides a method of preventing or reducing the severity of a stress-associated condition in a subject by systemically administering to the subject an effective amount of brimonidine or a pharmaceutically acceptable salt, ester, amide, stereoisomer or racemic mixture thereof. Stress-associated conditions that can be treated according to a method of the invention include, but are not limited to, dyspepsia, tachycardias other than tachycardia associated with myocardial ischemia, panic attack, non-inflammatory dermatological conditions, disorders of muscle contraction, sensory hypersensitivity associated with migraine, and behavioral disorders.

1 Claim, 7 Drawing Sheets

METHODS OF PREVENTING AND REDUCING THE SEVERITY OF STRESS-ASSOCIATED CONDITIONS

This application is a continuation of U.S. application Ser. No. 10/607,439, filed Jun. 25, 2003, now abandoned the contents of which are incorporated by reference herein.

BACKGROUND OF THE INVENTION

1. Field of the Invention

The invention relates generally to the sympathetic nervous system and various stress-associated conditions and, in particular, to the α-2 adrenergic agonist, brimonidine.

2. Background Information

Conditions that are associated with or exacerbated by stress can be mediated, at least in part, by the sympathetic nervous system. Such stress-associated conditions include, without limitation, gastrointestinal disease; irritable bowel syndrome; dyspepsia; tachycardia; panic attack; insulin-resistance; type II diabetes; dermatological conditions; disorders of muscle contraction such as tension type headache; sensory hypersensitivity associated with migraine such as nausea, photophobia and phonophobia; and stress-associated behavioral disorders such as overeating and drug dependence.

Unfortunately, treatments for such stress-associated conditions have generally been ineffective or unsatisfactory, for example, due to unwanted side-effects such as sedation. Thus, there is a need for novel methods of preventing or reducing the severity of stress-associated conditions. The present invention satisfies this need and provides related advantages as well.

SUMMARY OF THE INVENTION

The present invention provides a method of preventing or reducing the severity of a stress-associated condition in a subject by systemically administering to the subject an effective amount of brimonidine or a pharmaceutically acceptable salt, ester, amide, stereoisomer or racemic mixture thereof, where the stress-associated condition is one of the following: gastrointestinal disease; irritable bowel syndrome; dyspepsia; tachycardia; panic attack; insulin-resistance; type II diabetes; a non-inflammatory dermatological condition; a disorder of muscle contraction; sensory hypersensitivity associated with migraine; or a stress-associated behavioral disorder.

In one embodiment, a method of the invention prevents or reduces the severity of gastrointestinal disease. In other embodiments, a method of the invention prevents or reduces the severity of irritable bowel syndrome or dyspepsia. In another embodiment, a method of the invention prevents or reduces the severity of tachycardia other than tachycardia associated with myocardial ischemia, for example, tachycardia associated with a pulmonary disorder. In a further embodiment, a method of the invention prevents or reduces the severity of panic attack. In still further embodiments, a method of the invention prevents or reduces the severity of insulin-resistance, or prevents or reduces the severity of type II diabetes. In yet a further embodiment, a method of the invention prevents or reduces the severity of a non-inflammatory dermatological condition. In other embodiments, a method of the invention prevents or reduces the severity of a disorder of muscle contraction such as a disorder of skeletal muscle contraction or a disorder of smooth muscle contraction, for example, a disorder of smooth muscle contraction associated with cystitis or associated with non-bacterial prostatitis or a disorder of muscle contraction associated with tension type headache. In another embodiment, a method of the invention prevents or reduces the severity of sensory hypersensitivity associated with migraine. In a further embodiment, a method of the invention prevents or reduces the severity of sensory hypersensitivity associated with a stress-associated behavioral disorder. In a method of the invention, an effective amount of brimonidine can be administered by any of a variety of methods including, but not limited to, orally, topically, intravenously or via a patch.

DETAILED DESCRIPTION OF THE INVENTION

Figure 1:
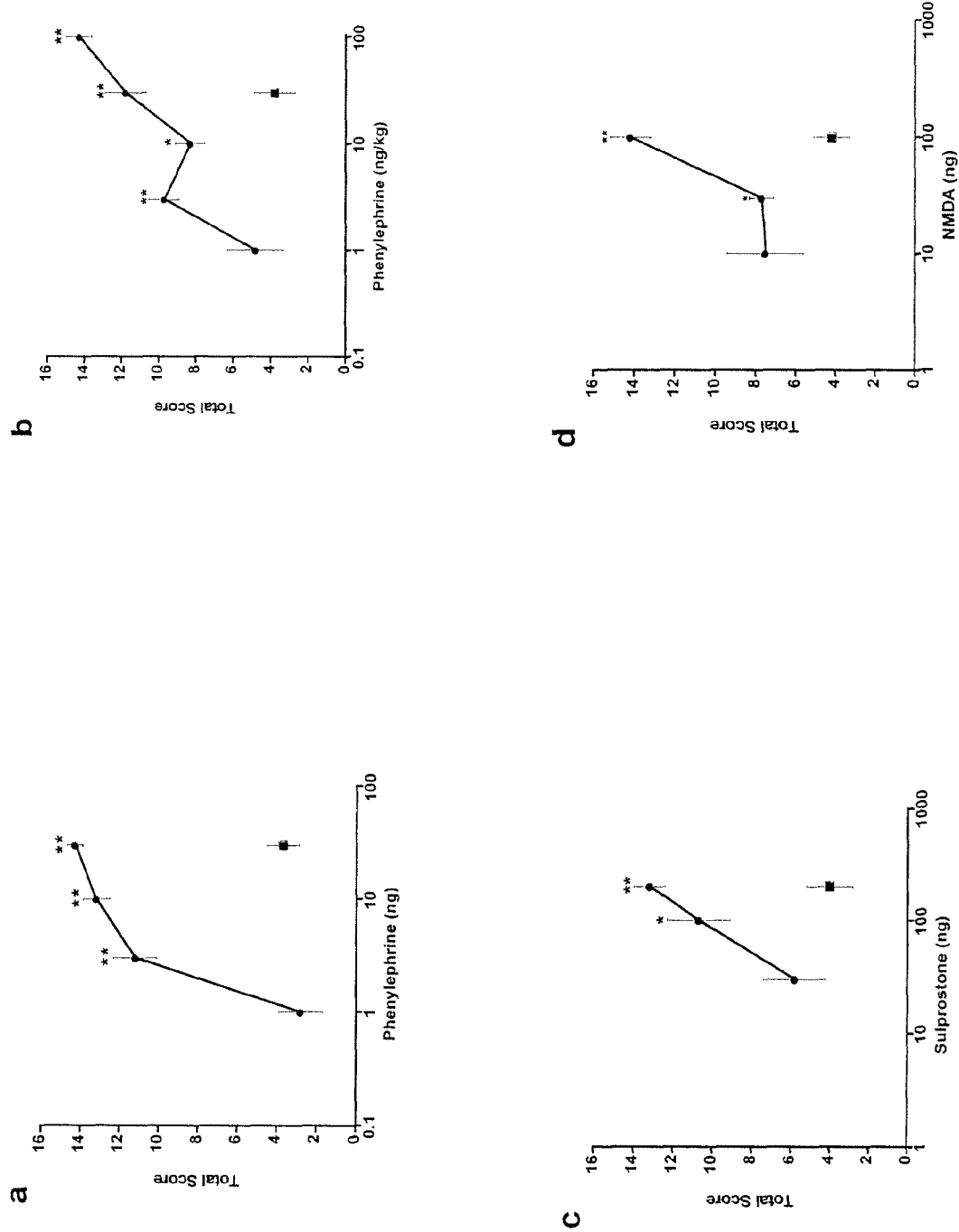
FIG. 1 shows the tactile hypersensitivity observed with several distinct chemical models. Each experimental group included 5-6 wildtype mice. Tactile hypersensitivity was assessed as described below; sensitization scores determined every 5 minutes during the 35 minute measurement period were summed and calculated as the mean +/−SEM. Each group was compared to a vehicle control using an unpaired two-tailed t-test (* $p<0.01$, ** $p<0.001$). (a) Spinal injection of the α-1 agonist, phenylephrine, induces tactile hypersensitivity in a dose dependent fashion. Phenylephrine (filled circle) was injected intrathecally at various doses. The α-1 antagonist, 5-MU (30 ug/kg i.p.; filled square) was administered 15 minutes prior to intrathecal administration of 30 ng phenylephrine. (b) Systemic phenylephrine induces tactile hypersensitivity in a dose dependent fashion. Phenylephrine (filled circle) was injected intraperitoneally at various doses. The α-1 antagonist, 5-MU (30 ug/kg i.p.; filled square) was administered 15 minutes prior to administration of 30 ng/kg phenylephrine. (c) Spinal sulprostone, a selective $EP_1/EP_3$ agonist, induces chemical tactile hypersensitivity in a dose responsive fashion. Increasing doses of sulprostone (filled circle) were injected intrathecally. An $EP_1$ antagonist (100 ng i.t.; filled square) was injected 15 minutes prior to administration of 200 ng sulprostone. (d) Spinal administration of NMDA induces tactile hypersensitivity in a dose responsive fashion. NMDA (filled circle) was injected intrathecally at various doses. The NMDA antagonist, memantine (1 ug i.t.; (filled square), was injected 15 minutes prior to administration of 100 ng NMDA.

Adrenergic receptors mediate physiological responses to the catecholamines, norepinephrine and epinephrine, and are members of the superfamily of G protein-coupled receptors having seven transmembrane domains. These receptors, which are divided pharmacologically into α-1, α-2 and β-adrenergic receptor types, are involved in diverse physiological functions including functions of the cardiovascular and central nervous systems. The α-adrenergic receptors mediate most excitatory functions: α-1 adrenergic receptors generally mediate responses in the effector organ, while α-2 adrenergic receptors are located postsynaptically as well as presynaptically, where they regulate release of neurotransmitters. Agonists of α-2 adrenergic receptors currently are used clinically in the treatment of hypertension, glaucoma, spasticity, and attention-deficit disorder, in the suppression of opiate withdrawal, and as adjuncts to general anesthesia.

α-2 adrenergic receptors are presently classified into three subtypes based on their pharmacological and molecular characterization: α-2A/D (α-2A in human and α-2D in rat); α-2B; and α-2C (Bylund et al., *Pharmacol. Rev.* 46:121-136 (1994); and Hein and Kobilka, *Neuropharmacol.* 34:357-366 (1995)). The α-2A and α-2B subtypes can regulate arterial contraction in some vascular beds, and the α-2A and (α-2C subtypes mediate feedback inhibition of norepinephrine release from sympathetic nerve endings.

The α-2A subtype also mediates many of the central effects of α-2 adrenergic agonists (Calzada and Artihano, *Pharmacol. Res.* 44: 195-208 (2001); Hein et al., *Ann. NY Acad. Science* 881:265-271 (1999); and Ruffolo (Ed.), α-*Adrenoreceptors: Molecular Biology, Biochemistry and Pharmacology* S. Karger Publisher's Inc. Farmington, Conn. (1991)).

Previous studies have shown that norepinephrine has a higher affinity for the α-2C receptor ($K_i$=650 nM) than the α-2A receptor ($K_i$=5800 nM; Link et al., *Mol. Pharm.* 42:16-27 (1992)). Thus, the autoinhibitory action on norepinephrine release is mediated through the α-2C receptor at low concentrations of norepinephrine, and through the α-2A receptor at high concentrations of norepinephrine (Altman et al., *Mol. Pharm.* 56:154-161 (1999)). As a result, feedback inhibition of basal norepinephrine release is mediated by the α-2C receptor, while the α-2A receptor mediates feedback inhibition of release under conditions of high frequency stimulation (Hein et al., *Ann. N.Y. Acad. Sci.* 881:265-271 (1999)). As disclosed herein in Example II, the α-2C knockout mice, which have a decreased presynaptic inhibition of sympathetic outflow under basal (or low frequency stimulation) conditions, are more sensitive to augmentation of α-1 receptor activity through phenylephrine treatment (see FIG. 2). Furthermore, as shown herein in FIG. 3, α-2A knockout mice are more sensitive to sulprostone-induced tactile hypersensitivity, while in α-2C knockout mice, the sulprostone sensitivity is the same as that of wildtype mice. These results demonstrate that sulprostone treatment results in high frequency sympathetic nerve stimulation, as evidenced by the fact that only α-2A knockout mice, which lack presynaptic inhibition of high frequency sympathetic outflow, exhibit a decreased threshold to sulprostone-induced tactile hypersensitivity.

Figure 5:
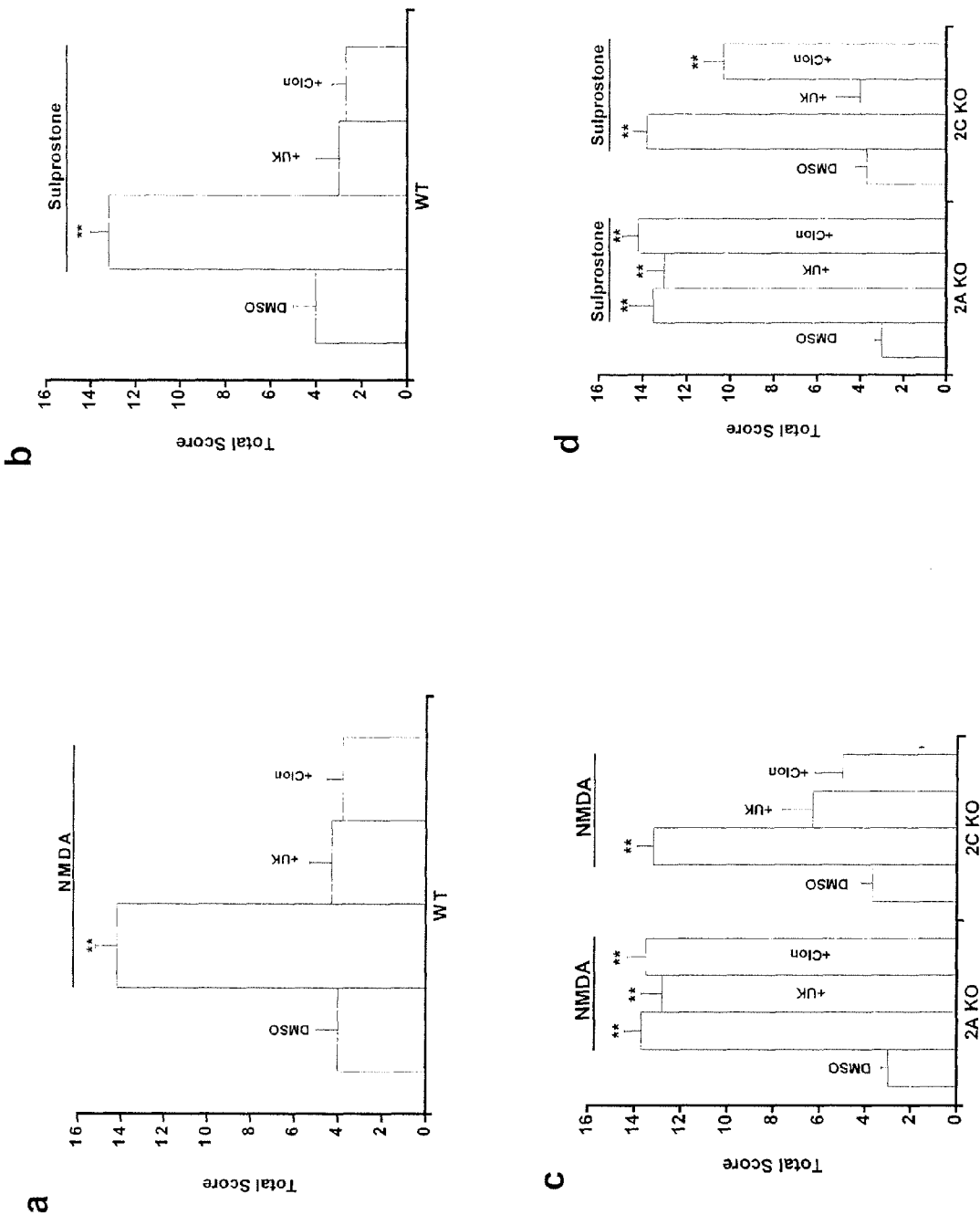
FIG. 5 shows that α-adrenergic agonists differ in alleviation of sympathetically-enhanced sensory hypersensitivity. The response of 5-6 mice per group was scored; the mean response and SEM were calculated as described above. Each drug-treated group was compared to a vehicle control group using an unpaired two-tailed t-test (* p<0.01, ** p<0.001). (a) Spinal brimonidine and clonidine alleviate NMDA-induced tactile hypersensitivity in wildtype mice. Mice were injected intrathecally with DMSO vehicle or co-injected intrathecally with 100 ng NMDA and saline, 0.4 µg brimonidine (UK14304) or 1 µg clonidine. (b) Spinal brimonidine and clonidine alleviate sulprostone-induced tactile hypersensitivity in wildtype mice. Mice were injected intrathecally with DMSO vehicle or co-injected intrathecally with 200 ng sulprostone and saline, 0.4 µg brimonidine (UK14304) or 0.4 µg clonidine. (c) Spinal brimonidine and clonidine alleviate NMDA-induced tactile hypersensitivity in the α-2C knockout mice, but not in the α-2A knockout mice. Mice were injected intrathecally with DMSO vehicle or coinjected intrathecally with 100 ng NMDA and saline, 0.4 µg brimonidine (UK14304) or 1 µg clonidine. (d) Spinal brimonidine and clonidine differ in their ability to alleviate sulprostone-induced tactile hypersensitivity in the α-2C knockout mice. Mice were injected with DMSO vehicle or co-injected intrathecally with 200 ng (α-2C knockout) or 30 ng (α-2A knockout) sulprostone and saline, 0.4 µg brimonidine (UK14304) or 0.4 µg clonidine. α-2 agonist analgesia is absent in the α-2A knockout mice; clonidine analgesia is also lost in the α-2C knockout mice.

As further disclosed herein in Example III, brimonidine was analgesic in both wild type and α-2C knockout mice with sulprostone-induced tactile hypersensitivity. In contrast, clonidine was analgesic in wild type mice but not in α-2C knockout mice (compare FIGS. 5b and d). As expected, neither clonidine nor brimonidine were analgesic in α-2A knockout mice, which lack the spinal α-2A adrenergic receptor which mediates analgesic activity. Thus, in α-2C knockout mice treated with sulprostone, which serve as a model for sympathetically-enhanced conditions, the pan-agonists brimonidine and clonidine have strikingly different activities. Additional results disclosed herein demonstrate that, in wild type mice, brimonidine, but not other pan-agonists such as tizanidine or clonidine, had analgesic activity without concomitant sedation (see FIG. 6). Furthermore, brimonidine was highly selective (more than 1000-fold)—for α-2 adrenergic receptors as compared to α-1 receptors in functional assays as compared to other pan-agonists such as clonidine and tizanidine, which exhibited less than 10-fold selectivity (see FIG. 7 and Table 2). These results demonstrate the differential functional activity of the pan-agonists brimonidine and clonidine and indicate that α-2 versus α-1 functional selectivity can be advantageous in treating sympathetically-enhanced conditions such as stress-associated conditions without concomitant sedation.

Dyspepsia has been described as a biopsychosocial disorder and is generally characterized, in part, by epigastric discomfort following meals. In addition to postprandial upper abdominal discomfort or pain, dyspepsia can be characterized by early satiety, nausea, vomiting, abdominal distension, bloating, or anorexia in the absence of organic disease (Thumshirn, *Gut* 51 Suppl. 1: i63-66 (2002; Anderson, *Dorland's Illustrated Medical Dictionary* 28$^{th}$ Edition, W.B. Saunder's Company, Philadelphia (1994)).

The methods of the invention can be useful for preventing or reducing the severity of dyspepsia, which, as used herein, is a term which means impaired digestion. Any of a variety of types of dyspepsia can be treated according to a method of the invention. The term dyspepsia includes, without limitation, acid dyspepsia, which is associated with excessive acidity of the stomach; appendicular dyspepsia, also known as appendix dyspepsia, in which dyspeptic symptoms accompany chronic appendicitis; catarrhal dyspepsia, which is accompanied by gastric inflammation; chichiko dyspepsia, a condition of farinaceous malnutrition found in poorly nourished infants; cholelithic dyspepsia, which involves sudden dyspeptic attacks associated with gallbladder disturbance; colonic dyspepsia, which involves a functional disturbance of the large intestine; fermentative dyspepsia, which is characterized by fermentation of ingested food; flatulent dyspepsia, which is associated with the formation of gas in the stomach and often involves upper abdominal discomfort accompanied by frequent belching; gastric dyspepsia, which originates in the stomach; and intestinal dyspepsia, which originates in the intestines. It is understood that these and other mildly or acutely symptomatic forms of the condition are included in the definition of "dyspepsia" as used herein. In one embodiment, the methods of the invention are used to prevent or reduce the severity of dyspepsia other than dyspepsia associated with gastric inflammation.

In another embodiment, the invention relates to treating gastrointestinal disease. Inflammatory bowel disease (IBD) or irritable bowel syndrome (IBS) are gastrointestinal diseases which affect one-half of all Americans during their lifetime, at a cost of greater than $2.6 billion dollars for IBD and greater than $8 billion dollars for IBS. The frequency or severity of visceral hypersensitivity associated with IBD, IBS and other gastrointestinal diseases including inflammatory gastrointestinal diseases is exacerbated by stress. As disclosed herein, the methods of the invention can be useful for preventing or reducing the severity of visceral hypersensitivity associated with a stress-associated gastrointestinal disease such as, without limitation, ulcerative colitis (UC), Crohn's disease (CD), or irritable bowel syndrome (IBS). Thus, the present invention provides a method of preventing or reducing the severity of visceral hypersensitivity associated with a stress-associated gastrointestinal disease in a subject by systemically administering to the subject an effective amount of brimonidine or a pharmaceutically acceptable salt, ester, amide, stereoisomer or racemic mixture thereof.

The methods of the invention also can be useful for preventing or reducing the severity of tachycardia which is not associated with myocardial ischemia. As used herein, the term "tachycardia" means excessive rapidity of heart rate and includes tachyarrhythmias. In adults, the term tachycardia generally refers to a heart rate of greater than 100 beats per minute. The term tachycardia encompasses tachycardias secondary to a variety of disorders other than myocardial ischemia including, without limitation, paroxysmal tachycardia, in which the tachycardia is of sudden onset and cessation and either ventricular or supraventricular, and nonparoxysmal tachycardia, which is a tachycardia of slow onset, generally with a heart rate of 70 to 130 beats per minute. In one embodiment, a method of the invention prevents or reduces the severity of an automatic tachycardia which is not associated with myocardial ischemia. In another embodiment, a method of the invention prevents or reduces the severity of tachycardia in an adult subject. In a further embodiment, a method of the invention prevents or reduces the severity of tachycardia in a subject who is a child.

Tachycardias to be treated according to a method of the invention include those originating from any part of the heart such as ventricular tachycardias and supraventricular tachycardias, which can be classified, for example, into atrial and junctional (nodal) tachycardias. Thus, the methods of the invention can be useful for preventing or reducing the severity of, for example, ventricular tachycardias, which are abnormally rapid ventricular rhythms with aberrant ventricular excitation, often in excess of 150 beats per minutes, generated within the ventricle and sometimes occurring in conjunction with atrioventricular dissociation. The methods of the invention further can be useful for preventing or reducing the severity of supraventricular tachycardias (SVT), which are regular tachycardias in which the point of stimulation is located above the bundle branches such as in the sinus node, atria or atrioventricular junction or which arise from a large reentrant circuit including both atrial and ventricular sites. In one embodiment, a method of the invention is used to prevent or reduce the severity of an atrial tachycardia, which is characterized by a rapid cardiac rate generally between 160 and 190 beats per minutes and which originates from an atrial locus; such tachycardias include, but are not limited to, paroxysmal atrial tachycardias. In another embodiment, a method of the invention is used to prevent or reduce the severity of a junctional tachycardia, which is a tachycardia arising in response to impulses originating in the atrioventricular junction and which is generally characterized by a heart rate greater than 75 beats per minute. Junctional tachycardias include nonparoxysmal and paroxysmal junctional tachycardias, such as junctional tachycardias resulting from reentry or enhanced automatically. It is understood that the methods also can be used to prevent or reduce the severity of, without limitation, double tachycardias, in which two types of ectopic tachycardia are involved; sinus tachycardias, which originate in the sinus node and can be associated with shock, hypotension, congestive heart failure or fever; orthostatic tachycardia, which is characterized by a disproportionate rapidity of heart rate upon rising from a reclining to a standing position; and chaotic atrial tachycardia, which is characterized by atrial rates of 100 to 130 beats per minute, markedly variable P wave morphology and irregular P-P intervals (Anderson, supra, 1994).

Tachycardias to be treated according to a method of the invention can be associated with one or more disorders such as pulmonary disease, diabetes, or surgical trauma and can occur, for example, in the elderly. As an example, chaotic atrial tachycardia (multifocal atrial tachycardia) can be present, for example, in patients with chronic obstructive pulmonary disease, in patients with diabetes, and in the elderly. As a further example, nonparoxysmal junctional tachycardia can be associated, for example, with surgical trauma. It is understood that these and a variety of well known automatic and other tachycardias which are not associated with myocardial ischemia can be prevented or reduced in severity according to the methods of the invention. In another embodiment, the invention provides a method of preventing or reducing the severity of tachycardias of all types including those associated with myocardial ischemia.

The methods of the invention also can be useful for preventing or reducing the severity of panic attack, a common disorder with a prevalence of around 3% in the general population (Potokar and Nutt, *Int. J. Clin. Pract.* 54: 110-114 (2000)). Panic disorder involving recurrent panic attacks is typically observed in young adults, with an average age of onset of 24 years, and is more common in females than in males. The term "panic attack," as used herein, means a discrete period of intense fear or discomfort accompanied by one or more of the following symptoms: accelerated heart rate or palpitation; chest pain; chills or hot flushes; derealization or depersonalization; fear of dying; fear of losing control or going crazy; dizziness or faintness; feelings of choking; nausea or abdominal distress; paraesthesia; sensations of shortness of breath or smothering; sweating; or trembling or shaking. A panic attack typically begins with the sudden onset of intense apprehension or fear and generally has a duration of about 5 to 20 minutes. The term panic attack encompasses both full-blown and limited-symptom attacks; full-blown attacks involve four or more of the above symptoms while limited-symptom attacks involve fewer than four symptoms. A method of the invention can entirely prevent a panic attack, or can prevent or reduce the severity of one or any combination of the attendant symptoms described above.

Some patients with panic attacks develop "panic disorder," which also can be prevented or reduced in severity using brimonidine according to a method of the invention. The term panic attack, as used herein, encompasses panic disorder, which is defined as recurrent panic attacks in conjunction with persistent concern over additional episodes or the consequences of the attacks or a notable change in behavior experienced for at least one month following one or more panic attacks. Panic disorder can be associated with other psychiatric conditions such as depression.

The central sympathetic nervous system can play a critical role in the development of insulin-resistance and hypertension which characterize type II diabetes (Rocchini et al., *Hypertension* 33[part II]:548-553 (1999)). Further provided herein is a method of preventing or reducing the severity of type II diabetes, a disorder characterized by hypertension, hyperlipidemia and insulin-resistance and which is exacerbated by stress. As disclosed herein, brimonidine or a pharmaceutically acceptable salt, ester, amide, stereoisomer or racemic mixture thereof, can be systemically administered to a subject in order to prevent or reduce the severity of type II diabetes in the subject.

The methods of the invention also can be useful for preventing or reducing the severity of a non-inflammatory dermatological condition. Such methods can be useful, for example, for preventing or reducing the severity of one or more symptoms such as itching or other discomfort associated with a non-inflammatory dermatological condition. As used herein, the term "non-inflammatory dermatological condition" means any dermatosis or other skin disease or condition that is not caused or accompanied by inflammation. A non-inflammatory dermatological condition to be treated according to a method of the invention can originate or be exacerbated under stressful conditions. Non-inflammatory dermatological conditions encompass, without limitation, non-inflammatory dermatoses including non-inflammatory blistering diseases such as epidermolysis bullosa and porphyria; ichthyosis; keratosis pilaris; juvenile plantar dermatosis (JPD); lichen plantus dermatosis; and xerosis. One skilled in the art understands that these and other non-inflammatory dermatological conditions known in the art can be treated by a method disclosed herein.

In a separate embodiment, the invention provides a method of preventing or reducing the severity of a stress-associated inflammatory dermatological condition in a subject by systemically administering to the subject an effective amount of brimonidine or a pharmaceutically acceptable salt, ester, amide, stereoisomer or racemic mixture thereof. Such methods can be useful, for example, in preventing or reducing the severity of one or more symptoms such as itching or other discomfort associated with the inflammatory dermatological condition. Any of a variety of inflammatory dermatological conditions are encompassed by the methods of the invention including, without limitation, any of a variety of forms of acute or chronic dermatitis such as psoriasis, allergic dermatitis such as allergic contact dermatitis, atopic dermatitis, dermatitis calorica, contact dermatitis, cosmetic dermatitis, eczema, exfoliative dermatitis, factitial dermatitis, irritant dermatitis, lichen simplex chronicus, marine dermatitis, neurodermatitis, perioral dermatitis, phototoxic dermatitis, seborrheic dermatitis, stasis dermatitis and dermatitis vegetans.

The methods of the invention can be useful for preventing or reducing the severity of a variety of disorders of muscle contraction, which are conditions that result, at least in part, from inappropriate muscle contraction. Disorders of muscle contraction to be treated according to a method of the invention include, without limitation, disorders of skeletal muscle contraction, disorders of smooth muscle contraction, disorders of muscle contraction associated with a gland, and disorders of cardiac muscle contraction such as congestive heart failure; these and other disorders to be prevented or reduced in severity-according to a method of the invention include those in which the myocytes are innervated as well as those in which the myocytes are not innervated. As non-limiting examples, the methods of the invention can be useful for preventing or reducing the severity of a disorder of muscle contraction such as back or other muscle spasm; muscle contraction associated with cystitis; muscle contraction associated with non-bacterial prostatitis; muscle contraction associated with teeth grinding; muscle contraction associated with tension type headache; and muscle contraction associated with congestive heart failure.

The methods of the invention can be useful, for example, for preventing or reducing the severity of a muscle spasm such as a back spasm. Muscle spasms are well known in the art. As used herein, the term "spasm" means a sudden, involuntary contraction of a muscle or a group of muscles, accompanied by pain and interference with function. A spasm can produce, for example, involuntary movement or distortion. In one embodiment, a method of the invention prevents or reduces the severity of a back spasm.

In one embodiment, a method of the invention is useful for preventing or reducing the severity of muscle contraction associated with cystitis. As used herein, the term "cystitis" means inflammation of the urinary bladder. The term cystitis encompasses, yet is not limited to, allergic cystitis, bacterial cystitis, acute catarrhal cystitis, cystic cystitis, diphtheritic (croupous) cystitis, eosinophilic cystitis, exfoliative cystitis, cystitis follicularis, cystitis glandularis, incrusted cystitis, chronic interstitial (panmural, submucous) cystitis, mechanical cystitis, cystitis papillomatosa and cystitis senilis feminarum. See, for example, Anderson, supra, 1994. Cystitis can be accompanied by one or more of the following clinical symptoms: frequent urination, burning on urination, suprapubic discomfort, lassitude, cloudy or blood-tinged urine and sometimes low-grade fever (Bennett and Plum (Eds.), *Cecil Textbook of Medicine* Sixth Edition, W.B. Saunders Company, Philadelphia 1996). One skilled in the art understands that the muscle contraction associated with any of these or other forms of mild, severe, acute or chronic cystitis can be treated according to a method of the invention.

As disclosed herein, a method of the invention also can be useful for preventing or reducing the severity of muscle contraction associated with non-bacterial prostatitis. Symptoms of prostatic inflammation are experienced by about 50% of men in adult life; of these, about 95% result from factors other than bacterial infection. As used herein, the term "non-bacterial prostatitis" is synonymous with "a bacterial prostatitis" and means inflammation of the prostate not resulting from bacterial infection. Non-bacterial prostatitis encompasses, yet is not limited to, chronic non-bacterial prostatitis, allergic or eosinophilic prostatitis and non-specific granulomatous prostatitis. It is understood that the term non-bacterial prostatitis includes, without limitation, prostatitis of unknown etiology characterized by abnormal expressed prostatic secretions (EPS) and normal bacterial cultures. In some cases, non-bacterial prostatitis can be effectively treated with antibiotics or stress management (Bennett and Plum, supra, 1996). It is understood that muscle contraction associated with these or other forms of mild, severe, acute or chronic non-bacterial prostatitis can be treated according to a method of the invention.

In another embodiment, a method of the invention is useful for preventing or reducing the severity of muscle contraction associated with tension type headache (TTH), which is a common form of headache affecting as many as 90% of adult Americans. As used herein, the term "tension type headache" means a headache caused, at least in part, by muscle contraction, which may be triggered, for example, by stress or exertion. The term "tension type headache" encompasses episodic and chronic headache and includes but is not limited to common tension headaches. Tension type headaches generally involve the posterior of the head and neck, although they may also appear at the top or front of the skull and are further generally characterized by symmetry and a non-disabling severity. Although not all may be present, diagnostic features of tension type headache include bilateral pain; mild to moderate severity; pressing-like character with a stable profile; accentuation as the day progresses; possible high frequency such as daily or continuously; and relative rarity of migrainous features such as nausea, photosensitivity, photosensitivity and aggravation by physical activity such as head movement.

Tension type headaches result from tightening of muscles of the face, neck and scalp due, for example, to stress, overwork, eyestrain or poor posture. Such headaches can last for days or weeks and can cause pain of varying intensity. Tension type headaches occurring over an extended period of time such as several weeks or months are denoted chronic tension headaches and are encompassed by the term tension type headache as used herein.

Tension type headaches can be distinguished from migraines by the absence of vascular features and symptoms such as nausea, vomiting and sensitivity to light and the absence of an aura (Spira, *Austr. Family Phys.* 27: 597-599 (1998). The term tension type headache, which refers to headaches without a significant vascular component, is used in contradistinction to tension-vascular headaches, cluster headaches, migrainous headaches and other headaches with a major vascular component. However, the methods of the invention also can be useful for preventing or reducing the severity of sensory hypersensitivity associated with other headaches including, but not limited to, cervicogenic headache, post-traumatic headache, cluster headache and temporomandibular joint disorder (TMJ).

The methods of the invention also can be useful for preventing or reducing the severity of sensory hypersensitivity associated with migraine, a headache that plagues more than 10% of the population and that may be associated with a vascular component. In one embodiment, the methods of the invention prevent or reduce the severity of an ocular hypersensitivity associated with migraine, for example, photophobia. The methods of the invention are useful for preventing or reducing the severity of sensory hypersensitivity associated with any of a variety of forms of migraine including, but not limited to, migraine without aura ("MO"), migraine with aura ("MA"), and migrainous disorder. Sensory hypersensitivity to be prevented or reduced in severity according to a method of the invention further can be associated with, for example, abdominal migraine, acute confusional migraine, basilar (basilar artery) migraine, hemiplegic or familial hemiplegic migraine, fulgurating migraine, ocular (ophthalmic) migraine, opthalmoplegic migraine or retinal migraine. In addition, the methods of the invention can be useful for preventing or reducing the severity of sensory hypersensitivity associated with a migraine equivalent, in which there is a migraine aura without headache. Migraine auras are the abnormal visual, motor, psychic, paresthesic or other neurologic abnormalities that accompany a migraine. See Elrington, *J. Neurol. Neurosurg. Psychiatry* 72 Supple. II:ii10-ii15 (2002); Anderson, supra, 1994; Bennett and Plum, supra, 1996.

The methods of the invention can be useful for preventing or reducing the severity of one or more of a variety of types of sensory hypersensitivity associated with migraine. Such sensory hypersensitivity includes, but is not limited to, nausea; vomiting; diarrhea; photophobia (light intolerance); and phonophobia (noise intolerance). Such sensory hypersensitivity also includes visual abnormalities such as bright flashing lights (scintillation or fortification scotomata) or a monocular (retinal) visual abnormality or hemianoptic loss of vision; paresthesia (abnormal touch sensation) such as unilateral paresthesia; aphasia (loss of speech or comprehension); hemiparesis (muscular weakness or incomplete paralysis on one side of the body); hemisensory defect; or vertigo, ataxia (loss of muscular coordination) or diplopia. It is understood that the methods of the invention can be useful for preventing or reducing the severity of one of these or other types of sensory hypersensitivity occurring prior to, during, or subsequent to migraine headache, or occurring in the absence of headache as part of a migraine equivalent.

The methods of the invention also can be useful for preventing or reducing the severity of one or more of a variety of types of sensory hypersensitivity associated with other disorders such as fibromyalgia, also known a's fibrositis. Fibromyalgia is a disorder involving chronic, widespread musculoskeletal pain and tenderness at multiple sites in the absence of signs of connective tissue or other musculoskeletal disease. In particular, fibromyalgia is defined by pain or tenderness at 11 of 18 or more sites as defined by the American College of Rheumatology. Fibromyalgia frequently is associated with disturbed sleep, chronic fatigue, headaches and irritable bowel syndrome (Bennett and Plum, supra, 1996).

A variety of types of sensory hypersensitivity can be associated with fibromyalgia and can be prevented or reduced in severity according to a method of the invention, including, without limitation, hypersensitivity to light, noise, touch or odors, cold or heat intolerance, nausea or allergic-like symptoms such as rhinitis, itching, or rash in the absence of a true allergy. One skilled in the art understands that the methods of the invention can be useful for preventing or reducing the severity of any of these or other types of sensory hypersensitivity associated with fibromyalgia.

The methods of the invention further can be useful for preventing or reducing the severity of a stress-associated behavioral disorder, which is any behavioral disorder which is induced or exacerbated by stress. As non-limiting examples, a stress-associated-behavioral disorder can be a compulsive or repetitive detrimental behavior which is induced or exacerbated by stress such as, without limitation, over-eating or obesity, obsessive compulsive disorder (OCD), tics, Tourette syndrome (TS), alcohol use, drug use, gambling, self-inflicted injurious behavior such as scratching or hair-pulling, or sexual impotency or arousal. In one embodiment, the stress-associated behavioral disorder is a disorder other than drug use. In another embodiment, the stress-associated behavioral disorder is a disorder other than drug or alcohol use.

The methods of the invention further can be useful for preventing or reducing the severity of a stress-associated psychiatric disorder, which is any psychiatric disorder which is induced or exacerbated by stress. As a non-limiting example, the methods of the invention can be used to prevent or reduce the severity of a psychiatric disorder such as schizophrenia.

Also provided herein is a method of preventing or reducing the severity of an ocular condition in a subject by systemically administering to the subject an effective amount of brimonidine or a pharmaceutically acceptable salt, ester, amide, stereoisomer or racemic mixture thereof. As disclosed herein, brimonidine can act as a neuroprotective agent, preventing, for example, retinal damage in a number of ocular conditions affecting the neurosensory retina. Ocular conditions which can be prevented or reduced in severity using brimonidine according to a method of the invention include, without limitation, diabetic retinopathy; macular edema such as macular edema associated with diabetes mellitus or other conditions; retinal degeneration such as age-related macular degeneration or retinitis pigmentosa; inflammatory disorders of the retina; vascular occlusive conditions of the retina such as retinal vein occlusions or branch or central retinal artery occlusions; retinopathy of prematurity; retinopathy associated with blood disorders such as sickle cell anemia; damage following retinal detachment; damage or insult due to vitrectomy surgery or retinal surgery; and other retinal damage including therapeutic damage such as that resulting from laser treatment of the retina, for example, pan-retinal photocoagulation for diabetic retinopathy or photodynamic therapy of the retina, for example, for age-related macular degeneration as well as other ocular conditions such as ocular itch. Ocular conditions that can be prevented or reduced in severity according to a method of the invention further include, without limitation, genetic and acquired optic neuropathies such as optic neuropathies characterized primarily by loss of central vision, for example, Leber's hereditary optic neuropathy (LHON), autosomal dominant optic atrophy (Kjer disease) and other optic neuropathies such as those involving mitochondrial defects, aberrant dynamin-related proteins or inappropriate apoptosis. See, for example, Carelli et al., *Neurochem. Intl.* 40:573-584 (2002); and Olichon et al., *J. Biol. Chem.* 278:7743-7746 (2003).

Figure 6:
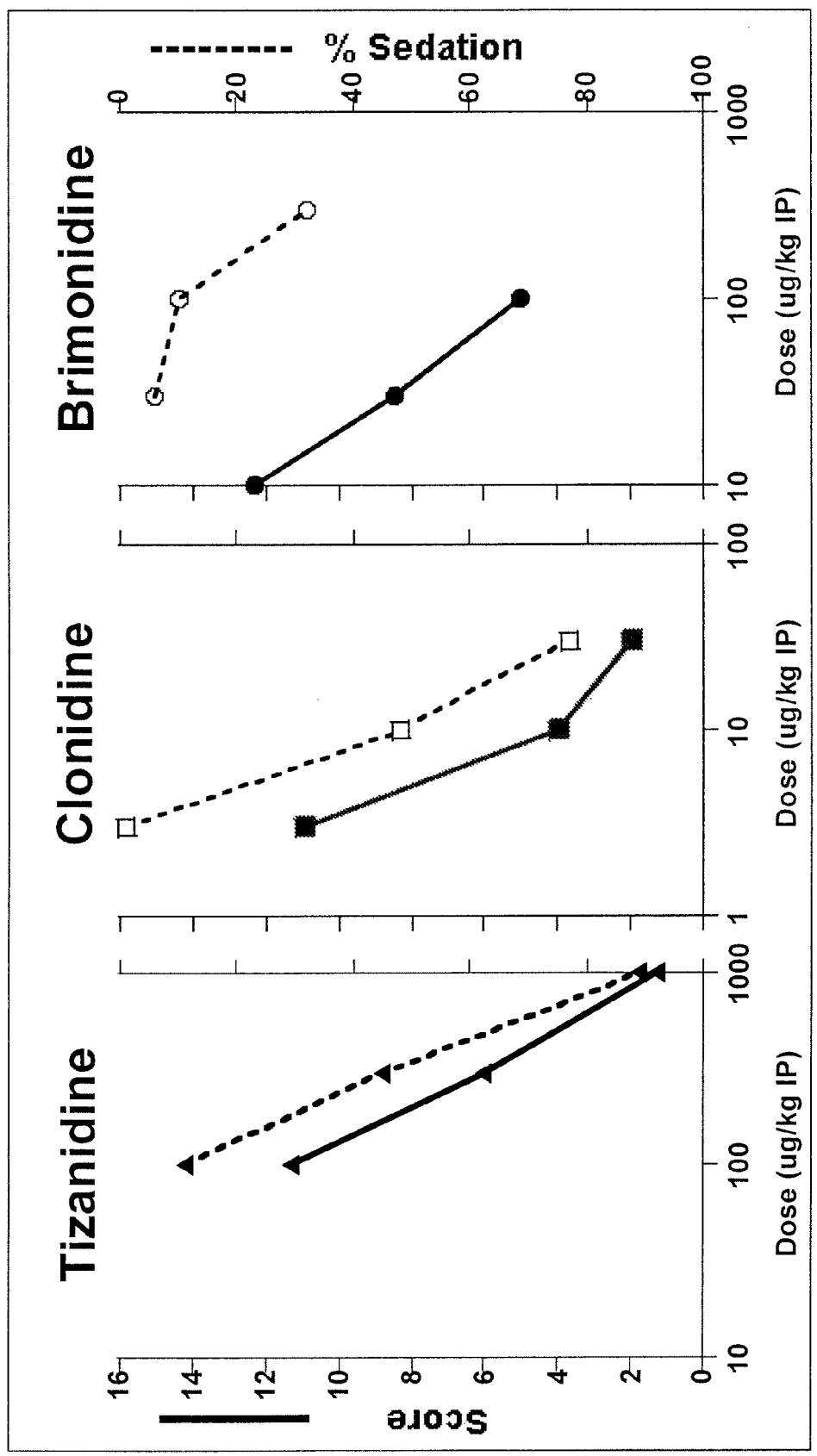
FIG. 6 shows that brimonidine, but not clonidine or tizanidine, alleviates sulprostone-induced tactile hypersensitivity in the absence of sedation. The dose-responsive anti-hypersensitive and sedative effects of three α-2 agonists (tizanidine, triangle; clonidine, square; and brimonidine, circle) were compared in models of sulprostone-induced tactile hypersensitivity and locomotor activity, respectively. The mean total sensitivity scare and standard error of the mean was calculated and indicated as a solid line (left axis). Locomotor activity relative to vehicle-treated animals was expressed as a percentage, and the percent sedation calculated as 100% minus the percent locomotor activity and indicated as a hatched line (right axis).
Figure 7:
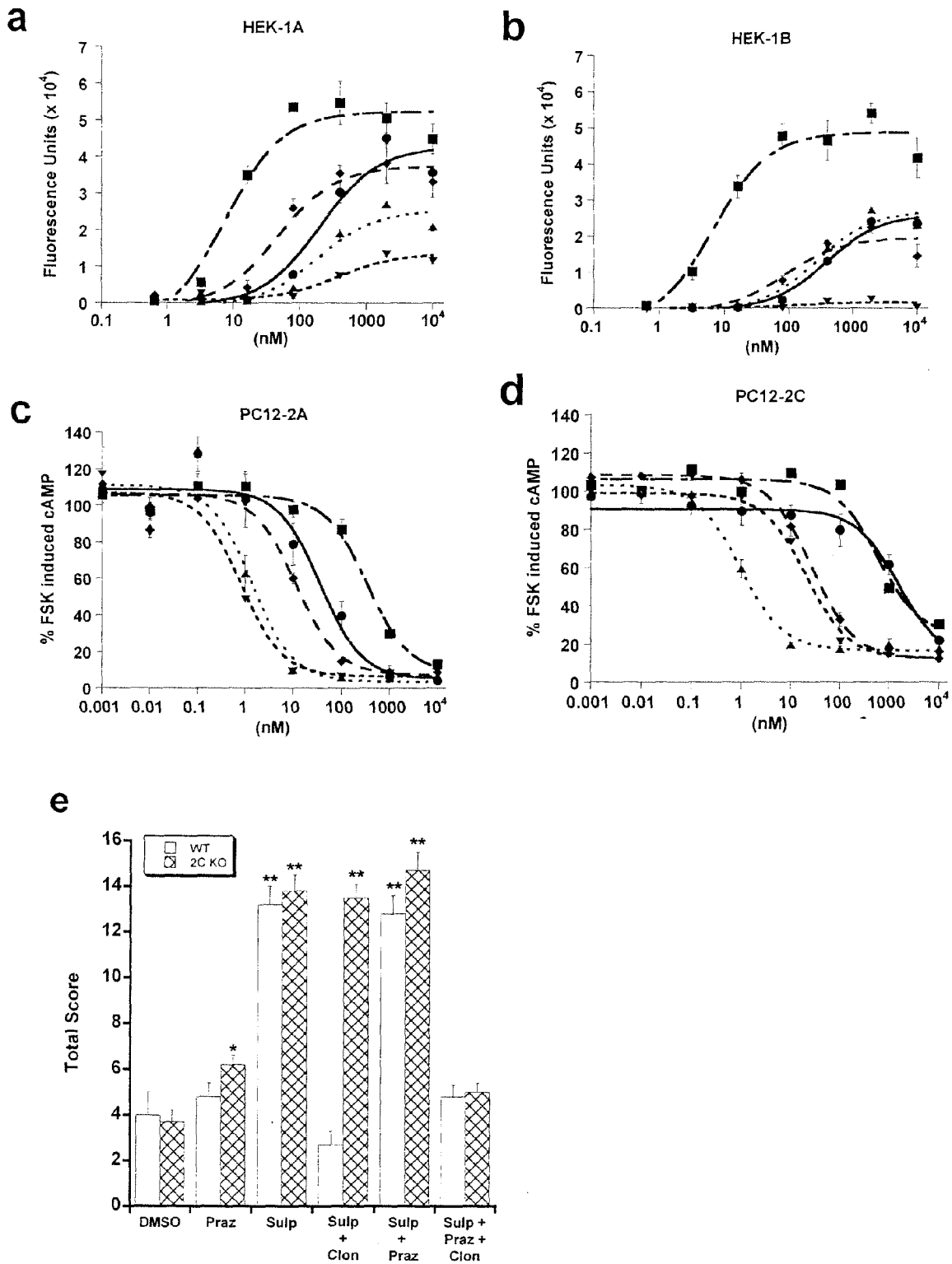
FIG. 7 shows variable α-2 vs. α-1 agonist selectivity in α-adrenergic agonists clonidine and brimonidine. Increasing concentrations of phenylephrine (filled square), clonidine (filled diamond), tizanidine (filled circle), dexmeditomidine (filled triangle) and brimonidine (filled inverted triangle) were tested for α-1 and α-2 agonist activity using in vitro cell-based functional assays. (a, b) α-1A and α-1B agonist activity of α-adrenergic agonists. The increase in intracellular calcium in HEK cells stably expressing the bovine α-1A receptor (a) or the hamster α-1B receptor (b) following addition of various concentrations of α-adrenergic agonists was determined by measuring the change in fluorescence of a calcium-sensitive dye. Agonists were tested 6-15 times in triplicate, and the mean fluorescence and SEM calculated at each concentration. Results from a typical experiment are shown. (c, d) α-2A and α-2C agonist activity of α-adrenergic agonists. Inhibition of forskolin-induced cAMP accumulation in PC12 cells stably expressing the human α-2A receptor (c) or the human α-2C receptor (d) following addition of various-concentrations of α-adrenergic agonists. Agonists were tested 3-5 times in triplicate, and the mean % inhibition and SEM calculated at each concentration. Results from a typical experiment are shown. (e) Co-administration of prazosin with clonidine restores clonidine-mediated analgesia in α-2C knockout mice. Wildtype (open bars) and α-2C knockout (hatched bars) mice were injected with vehicle, prazosin (100 ng/kg i.p.), sulprostone (200 ng i.t.), clonidine (400 ng i.t.) or various combinations as indicated. The tactile hypersensitivity of 5-6 mice per group was scored, and the mean response and SEM was calculated. Each drug-treated group was compared to a vehicle control group using an unpaired two-tailed t-test (* p<0.01, +* p<0.001).

The methods of the invention can be useful for preventing or reducing the severity of a stress-associated condition without concomitant sedation. Sedation, as used herein, is a term that means a reduction in motor activity. The phrase "without concomitant sedation," as used herein, means that relatively little reduction in motor activity accompanies the reduction in severity of one or more symptoms of a stress-associated condition at one or more doses of drug. A drug generally acts "without concomitant sedation" if, upon peripheral administration, the dose required to produce a 20% reduction in motor activity is at least 3-fold greater than the dose required to produce a significant reduction in one or more symptoms of the stress-associated condition. As shown in FIG. 6, brimonidine but not tizanidine or clonidine could be administered at doses that produced a reduction in the sensitization score (solid line, left axis) with less than a 20% increase in sedation (broken line, right axis). As non-limiting examples, the dose required to produce a 20% reduction in motor activity can be at least 4-fold greater than, 5-fold greater than, 6-fold greater than, 7-fold greater than, 8-fold greater than, 9-fold greater than, 10-fold greater than, 25-fold greater than, 50-fold greater than, 100-fold greater than, 200-fold greater than, 500-fold greater than, 1000-fold greater than, 2000-fold greater than, or 5000-fold greater than the dose required to produce a significant reduction in one or more symptoms of a stress-associated condition. Methods of determining the extent of a reduction in severity of symptoms of a stress-associated condition and the extent of sedation are well known in the art.

The term "brimonidine" as used herein, means a compound having the formula

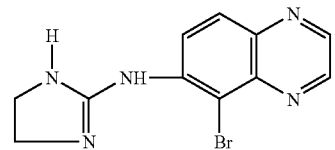

or a pharmaceutically acceptable derivative thereof such as a salt, ester, amide, stereoisomer, racemic mixture, polymorph, hydrate or solvate. Such a pharmaceutically acceptable derivative can have substantially the activity of 5-bromo-6-(2-imidazolin-2-ylamino)quinoxaline D-tartrate (1:1) in reducing tactile hypersensitivity without concomitant sedation in sulprostone-treated mice. The term brimonidine encompasses, without limitation, Alphagan™ and UK14304. Brimonidine, and pharmaceutically acceptable salts, esters, amides, stereoisomers and racemic mixtures thereof, is commercially available, for example, as Alphagan™ (Allergen). In addition, brimonidine and pharmaceutically acceptable salts, esters, amides, stereoisomers and racemic mixtures thereof can be prepared by routine methods as described below in Example I. See, also, U.S. Pat. No. 6,323,204.

Thus, it is understood that the methods of the invention encompass the use of pharmaceutically acceptable salts, esters and amides derived from the formula representing brimonidine. Suitable pharmaceutically acceptable salts of brimonidine include, without limitation, acid addition salts, which can be formed, for example, by mixing a solution of brimonidine with a solution of an appropriate acid such as hydrochloric acid, sulfuric acid, fumaric acid, maleic acid, succinic acid, acetic acid, benzoic acid, citric acid, tartaric acid, carbonic acid or phosphoric acid. Pharmaceutically acceptable salts further include, yet are not limited to, acid phosphate, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroiodide, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium, oleate, oxalate, pamoate (embonate), palmitate, pantothenate, phosphate/diphosphate, polygalacturonate, saccharate, salicylate, stearate, sulfate, subacetate, succinate, tannate, tartrate, teoclate, p-toluene sulphonate salts, tosylate, triethiodide and valerate. In one embodiment, a method of the invention is practiced with brimonidine tartrate.

It further is understood that functional groups of brimonidine can be modified, for example, to enhance the pharmacological utility of the compound. Such modifications, which are well within the knowledge of the skilled chemist and include, without limitation, esters, amides, ethers, N-oxides, and pro-drugs of brimonidine, are encompassed within the term "brimonidine" as used herein. Examples of modifications that can enhance activity include, for example, esterification such as the formation of $C_1$ to $C_6$ alkyl esters, preferably $C_1$ to $C_4$ alkyl esters, wherein the alkyl group is a straight or branched chain. Other acceptable esters include, for example, $C_5$ to $C_7$ cycloalkyl esters and arylalkyl esters such as benzyl esters. Such esters can be prepared from the compounds described herein using conventional methods well known in the art of organic chemistry.

Other pharmaceutically acceptable modifications include the formation of amides. Useful amide modifications include, for example, those derived from ammonia; primary $C_1$ to $C_6$ dialkyl amines, where the alkyl groups are straight or branched chain; and arylamines having various substitutions. In the case of secondary amines, the amine also can be in the form of a 5 or 6 membered ring. Methods for preparing these and other amides are well known in the art.

It is further understood that chemically distinct enantiomers and tautomers of brimonidine are encompassed within the term "brimonidine" and can be useful in the methods of the invention. Furthermore, in crystalline form, a compound may exist as polymorphs; in the presence of a solvent, a compound may form a solvate, for example, with water or a common organic solvent. Such polymorphs, hydrates and other solvates of brimonidine also are encompassed within the term "brimonidine" and can be useful in the methods of the invention disclosed herein.

It is understood that pharmaceutical compositions containing brimonidine can be useful in the methods of the invention. Such a pharmaceutical composition includes brimonidine and optionally includes an excipient such as a pharmaceutically acceptable carrier or a diluent, which is any carrier or diluent that has substantially no long term or permanent detrimental effect when administered to a subject. An excipient generally is mixed with active compound, or permitted to dilute or enclose the active compound. A carrier can be a solid, semi-solid, or liquid agent that acts as an excipient or vehicle for the active compound. Examples of solid carriers include, without limitation, pharmaceutical grades of mannitol, lactose, starch, magnesium stearate, sodium saccharin, polyalkylene glycols, talcum, cellulose, glucose, sucrose and magnesium carbonate. Suppository formulations can include, for example, propylene glycol as a carrier. Examples of pharmaceutically acceptable carriers and diluents include, without limitation, water, such as distilled or deionized water; saline; aqueous dextrose, glycerol, ethanol and the like. It is understood that the active ingredients can be soluble or can be delivered as a suspension in the desired carrier or diluent.

A pharmaceutical composition also can optionally include one or more agents such as, without limitation, emulsifying agents, wetting agents, sweetening or flavoring agents, tonicity adjusters, preservatives, buffers or anti-oxidants. Tonicity adjustors useful in a pharmaceutical composition include, but are not limited to, salts such as sodium acetate, sodium chloride, potassium chloride, mannitol or glycerin and other pharmaceutically acceptable tonicity adjustors. Preservatives useful in pharmaceutical compositions include, without limitation, benzalkonium chloride, chlorobutanol, thimerosal, phenylmercuric acetate, and phenylmercuric nitrate. Various buffers and means for adjusting pH can be used to prepare a pharmaceutical composition, including, but not limited to, acetate buffers, citrate buffers, phosphate buffers and borate buffers. Similarly, anti-oxidants useful in pharmaceutical compositions are well known in the art and include, for example, sodium metabisulfite, sodium thiosulfate, acetylcysteine, butylated hydroxyanisole and butylated hydroxytoluene. It is understood that these and other substances known in the art of pharmacology can be included in a pharmaceutical composition useful in the methods of the invention. See, for example, Remington's *Pharmaceutical Sciences* Mack Publishing Company, Easton, Pa. $16^{th}$ Edition 1980. Furthermore, a composition containing brimonidine may be administered-in conjunction with one or more other therapeutic substances, in the same or different pharmaceutical composition and by the same or different routes of administration.

Brimonidine, or a pharmaceutically acceptable salt, ester, amide, stereoisomer or racemic mixture thereof, is administered in an effective amount. Such an effective amount generally is the minimum dose necessary to achieve the desired prevention or reduction in severity of one or more symptoms of a stress-associated condition, for example, that amount roughly necessary to reduce the discomfort caused by the stress-associated condition to tolerable levels. Such a dose generally is in the range of 0.1-1000 mg/day and can be, for example, in the range of 0.1-500 mg/day, 0.5-500 mg/day, 0.5-100 mg/day, 0.5-50 mg/day, 0.5-20 mg/day, 0.5-10 mg/day or 0.5-5 mg/day, with the actual amount to be administered determined by a physician taking into account the relevant circumstances including the severity and type of stress-associated condition, the age and weight of the patient, the patient's general physical condition, and the pharmaceutical formulation and route of administration. Suppositories and extended release formulations also can be useful in the methods of the invention, including, for example, dermal patches, formulations for deposit on or under the skin and formulations for intramuscular injection.

A pharmaceutical composition useful in the methods of the invention can be administered to a subject by a variety of means depending, for example, on the type of condition to be treated, the pharmaceutical formulation, and the history, risk factors and symptoms of the subject. Routes of administration suitable for the methods of the invention include both systemic and local administration. As non-limiting examples, a pharmaceutical composition useful for preventing or reducing the severity of a stress-associated condition can be administered orally; parenterally; by subcutaneous pump; by dermal patch; by intravenous, intra-articular, subcutaneous or intramuscular injection; by topical drops, creams, gels or ointments; as an implanted or injected extended release formulation; by subcutaneous minipump or other implanted device; by intrathecal pump or injection; or by epidural injection. Depending on the mode of administration, brimonidine can be incorporated in any pharmaceutically acceptable dosage form such as, without limitation, a tablet, pill, capsule, suppository, powder, liquid, suspension, emulsion, aerosol or the like, and can optionally be packaged in unit dosage form suitable for single administration of precise dosages, or sustained release dosage forms for continuous controlled administration.

A method of the invention can be practiced by peripheral administration of brimonidine, or a pharmaceutically acceptable salt, ester, amide, stereoisomer or racemic mixture thereof. As used herein, the term "peripheral administration" or "administered peripherally" means introducing brimonidine, or a pharmaceutically acceptable salt, ester, amide, stereoisomer or racemic mixture thereof, into a subject outside of the central nervous system. Peripheral administration encompasses any route of administration other than direct administration to the spine or brain.

Peripheral administration can be local or systemic. Local administration results in significantly more of a pharmaceutical composition being delivered to and about the site of local administration than to regions distal to the site of administration. Systemic administration results in delivery of a pharmaceutical composition essentially throughout at least the entire peripheral system of the subject.

Routes of peripheral administration useful in the methods of the invention encompass, without limitation, oral administration, topical administration, intravenous or other injection, and implanted minipumps or other extended release devices or formulations. A pharmaceutical composition useful in the invention can be peripherally administered, for example, orally in any acceptable form such as in a tablet, liquid, capsule, powder, or the like; by intravenous, intraperitoneal, intramuscular, subcutaneous or parenteral injection; by transdermal diffusion or electrophoresis; topically in any acceptable form such as in drops, creams, gels or ointments; and by minipump or other implanted extended release device or formulation.

The following examples are intended to illustrate but not limit the present invention.

EXAMPLE I

Preparation of Brimonidine

This example describes preparation of brimonidine (5-bromo-6-(2-imidazolin-2-ylamino) quinoxaline).

Preparation 6-Amino-5-bromoquinoxaline hydrobromide

6-Aminoquinoxaline (2.08 g, 14.4 mmol) was dissolved in 11.5 ml glacial acetic acid. The solution was cooled in water while a solution of bromine (0.74 ml, 2.3 g, 14.4 mmol) in 1.5 ml glacial acetic acid was added slowly over 15 minutes. After stirring for an additional 30 minutes, the orange red solid formed was filtered off and washed thoroughly with dry ether. The solid was dried in vacuo overnight to yield 4.44 g crude product (a yield of 100%). The compound, 6-amino-5-bromoquinoxaline hydrobromide, had no definite melting point. A phase change from fine powder to red crystals was observed at about 220° C. Decomposition was observed at about 245° C. The material was used directly for preparation of 6-amino-5-bromoquinoxaline as follows.

6-Amino-5-Bromoquinoxaline

Crude 6-amino-5-bromoquinoxaline from above was dissolved in water, and saturated sodium bisulfite solution was added until the resulting solution tested negative with starch-iodide paper. The solution was then basified with 2N sodium hydroxide and extracted thoroughly with ethyl acetate. The organic extract was dried over magnesium sulfate and concentrated under reduced pressure to give the free base. The crude product was recrystallized from boiling benzene to give yellow crystals, m.p. 155-6° C. Using various analytical procedures, the yellow crystals were determined to be 6-amino-5-bromoquinoxaline. The yield was 82%.

6-Bromo-6-isothiocyanatoquinoxaline

The crude hydrobromide product described above (4.27 g, 14.0 mmol) was dissolved in 60 ml of water; thiophosgene (Aldrich, 1.28 ml, 16.8 mmol) was added in small portions with vigorous stirring. After 2 hours, the red color of the solution was discharged. The solid formed was filtered off and washed thoroughly with water. After drying in vacuo at 25° C., 3.38 g of brick red crystals were obtained, m.p. 157-8° C., representing a yield of 90%. A portion of this material was further purified by column chromatography to give white crystals, m.p. 157-8° C. Using various analytical procedures, these crystals were determined to be 5-bromo-6-isothiocyanatoquinoxaline.

5-Bromo-6(-N-(2-aminoethyl)thioureido)quinoxaline

A solution of the isothiocyanate (3.25 g, 12.2 mmol) in 145 ml benzene was added to a solution of ethylenediamine (Aldrich, 5.43 g, 90.0 mmol) in 18 ml benzene at 25° C. over 2 hours. After stirring for a further 30 minutes, the supernatant was poured off. The oil which remained was washed by swirling with dry ether three times and used directly for the next step.

A portion of this product was further purified by column chromatography ($SiO_2$, $CHCl_3$) for characterization. A white solid was recovered which decomposed at 175° C. with gas evolution (puffing). This white solid was determined to be 5-bromo-6(—N-2-(aminoethyl)thioureido) quinoxaline.

5-Bromo-6-(2-imidazolin-2-ylamino) quinoxaline

The crude product from above was dissolved in 100 ml dry methanol and the brown solution was refluxed for 19 hours until hydrogen sulfide gas was no longer evolved. The mixture was cooled to room temperature and concentrated to about 50 ml. The yellow solid was filtered off and dried in vacuo; the solid weighed 2.52 g (a yield of 70%) and had a melting point of 242-4° C.

As the crude product was insoluble in most common organic solvents, initial purification was achieved by an acid-base extraction procedure. Crude product (23 g) was dissolved in 100 ml 0.5N hydrochloric acid. The turbid yellow solution was filtered to give a clear orange yellow solution which was extracted twice with ethyl acetate (10 ml each extraction). The aqueous phase was cooled to 0° C. and basified with 6N sodium hydroxide, keeping the temperature of the solution below 15° C. at all times. The yellow solid which precipitated was filtered off and washed thoroughly with water until the washings were neutral to pH paper. The solid was dried overnight in vacuo to give 1.97 g yellow solid, m.p. 249-250° C. The recovery was about 88%.

Further purification was achieved by recrystallization. The partially purified product from above was dissolved in N,N-dimethylformamide (about 17 ml/g) at 100° C. with vigorous stirring. The solution was filtered hot and set aside to cool overnight. The bright yellow crystals were collected by filtration, m.p. 252-253° C. Recovery was from 65-77%. Using various analytical procedures, the bright yellow solid was determined to be 5-bromo-6-(2-imidazolin-2-ylamino) quinoxaline.

EXAMPLE II

Mouse Models with Different Mechanisms of Sensory Sensitization

This example demonstrates that the increased sympathetic tone of α-2A and α-2C knockout mice enhances induction of tactile hypersensitivity by α-1 receptor activation.

A. Sulprostone-induced Tactile Hypersensitivity is Driven by the Sympathetic Nervous System while Phenylephrine-induced Tactile Hypersensitivity is Independent of Sympathetic Nervous System Input To dissect the contribution of the sympathetic nervous system to sensory sensitization, mouse models having different mechanisms of sensory sensitization were developed. Tactile hypersensitivity was measured in mice following intrathecal or intraperitoneal injection of an inducing agent by scoring the response to light stroking of the mouse flank with a paintbrush. To mimic increased sympathetic tone, phenylephrine, an α-1 adrenergic receptor agonist, was injected. As shown in FIGS. 1a and 1b, intrathecal (i.t.) or intraperitoneal (i.p.) dosing of phenylephrine caused tactile hypersensitivity, with significant responses observed starting at doses of 3 ng i.t. and 3 ng/kg i.p. Induction of tactile hypersensitivity was α-1 receptor dependent, as evidenced by the ability of the α-1 receptor antagonist 5-methyl urapidil (5-MU) to block the hypersensitive response when injected intraperitoneally.

The activity of a synthetic $EP_1/EP_3$ receptor-selective prostaglandin agonist, sulprostone, also was assayed. As shown in FIG. 1c, increasing doses of intrathecal sulprostone elicited dose-dependent tactile hypersensitivity; doses of 100 and 200 ng caused a significant hypersensitive response. Coadministration of a specific $EP_1$ receptor antagonist completely blocked the sulprostone-induced tactile hypersensitivity, demonstrating that sulprostone mediates tactile hypersensitivity through activation of the $EP_1$ receptor.

In a third mouse model, chemical sensitization was induced by injection of increasing intrathecal doses of NMDA, which may activate NMDA channels on post-synaptic dorsal horn neurons (Woolf et al., Science 288:1765-1769 (2000)). Intrathecal NMDA resulted in a dose-dependent tactile hypersensitivity with a maximal effect at a 100 ng dose. The hypersensitivity was blocked with the NMDA antagonist, memantine, as shown in FIG. 1d.

To assess whether the three stimuli sensitize sensory pathways by different mechanisms, a set of pharmacological agents was assayed for the ability to prevent or ameliorate tactile hypersensitivity. As shown in Table 1, each receptor antagonist (5-MU, the $EP_1$ receptor antagonist or memantine) blocked only tactile hypersensitivity resulting from the corresponding receptor agonist (phenylephrine, sulprostone or NMDA, respectively). Gabapentin, which is used clinically to alleviate neuropathic pain by reducing spinal sensitization, also was assayed for the ability to block tactile hypersensitivity. Gabapentin inhibited tactile hypersensitivity elicited by sulprostone and NMDA, but not by phenylephrine, further demonstrating differences between the sensory pathways involved by different stimuli.

TABLE 1

Receptor antagonists and clinically used analgesics inhibit chemically-induced mechanical hypersensitivity

|  | Vehicle | 5-MU | $EP_1$ antagonist | Memantine | Gabapentin |
|---|---|---|---|---|---|
| Phenylephrine (100 ng/kg I.P.) | 14.3 ± 0.7** | 5.0 ± 1.0 | 9.8 ± 0.7** | 11.0 ± 0.7** | 13.0 (±0.6)** |
| Sulprostone (200 ng IT) | 13.2 ± 0.8** | 12.0 ± 1.0** | 4.0 ± 1.2 | 14.3 ± 0.8** | 3.2 ± 0.5 |
| NMDA (100 ng IT) | 14.2 ± 1.0** | 13.3 ± 0.8** | 11.4 ± 1.53* | 4.2 ± 0.9 | 3.7 ± 0.8 |

*indicates $p < 0.01$

**indicates $p < 0.001$

α-2 knockout mice were provided by Dr. Brian Kobilka (Stanford University; Link et al., Mol. Pharmacol. 48:48-55 (1995); Altman et al., Mol. Pharmacol. 56:154-161 (1999)). The α-2 knockout mice have a C57BL/6 background and were bred from homozygous knockout mice breeding pairs. Age and sex matched C57BL/6 wildtype mice were used as controls.

Sulprostone (Cayman Chemical; Ann Arbor, Mich.) and NMDA (Sigma; St Louis, Mo.) were dissolved in dimethyl sulfoxide (DMSO). The $EP_1$ receptor antagonist

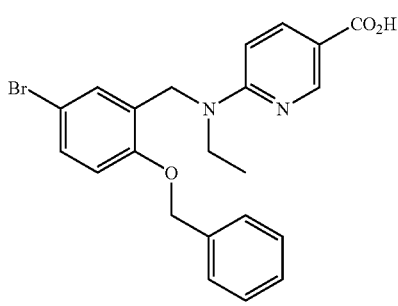

synthesized essentially as described in U.S. Pat. No. 5,843,942, and gabapentin (Victor Medical; Irvine, Calif.) were dissolved in 50% DMSO, 50% saline. Memantine (1-amino-3,5-dimethyladamantane hydrochloride), an analog of the well known anti-viral agent amantadine (1-adamantanamine hydrochloride), was synthesized essentially as described in U.S. Pat. No. 5,061,703 (see, also, Schneider et al., Dtsch Med. Wochenschr. 109:987 (1984)). 5-methylurapidil, brimonidine, phenylephrine, clonidine and guanethidine were obtained from Sigma and dissolved in saline. Prazosin (Sigma) and tizanidine (Biomol; Plymouth Meeting, Pa.) were dissolved in distilled water.

Spinal drug injections were performed as follows. Mice (20-30 g) were injected intrathecally as described in Hylden and Wilcox, Eur. J. Pharmacol. 67:313-316 (1980). Briefly, a sterile 30-gauge ½ inch needle attached to a microsyringe was inserted between the L5 and L6 vertebrae. The mouse was held firmly by the pelvic girdle in one hand, while the syringe was held in the other hand at an angle of approximately 20° above the vertebral column. The needle was inserted into the tissue to one side of the L6 spinous process, into the groove between the spinous and transverse processes. The needle angle was decreased to about 10°, and the needle slowly advanced forward into the intervertebral space until a pop was felt and there was a visible serpentine tail movement. Compounds were slowly injected in the subarachnoid space in a volume of 5 µl. Each compound was tested at multiple doses. The minimal efficacious dose was used for all subsequent experiments.

Sensitivity to light touch was quantified by scoring the response of mice to light stroking of their flanks with a small paintbrush, which is not normally painful. The mice were rated on the following scale once every 5 minutes between 15 and 50 minutes post injection: a score of "2" was given to animals showing-aggressive escape responses along with squeaking and biting at the brush; a score of "1" was given to animals exhibiting mild squeaking with attempts to escape; and a score of "0" was given if the animal showed no response to the light stroking of the paintbrush. The scores were summed to generate a cumulative score of 0 to 16 as described in Minami et al., Pain 57:217-223 (1994). Statistical calculations of significance for in vivo studies were done using a two-tailed Students t-test.

Guanethidine sympathectomies were performed essentially as follows. Animals were injected intraperitoneally with 50 mg/kg guanethidine (Malmberg and Basbaum, Pain 76:215-222 (1998)) before being assessed for baseline tactile sensitivity 24 hours later. Animals that exhibited normal tactile sensitivity were assayed for sensitivity to chemical induction of tactile hypersensitivity. Mice recovered from the sympathectomy six to eight days later as demonstrated by a return to pre-sympathectomy responsiveness.

Figure 2:
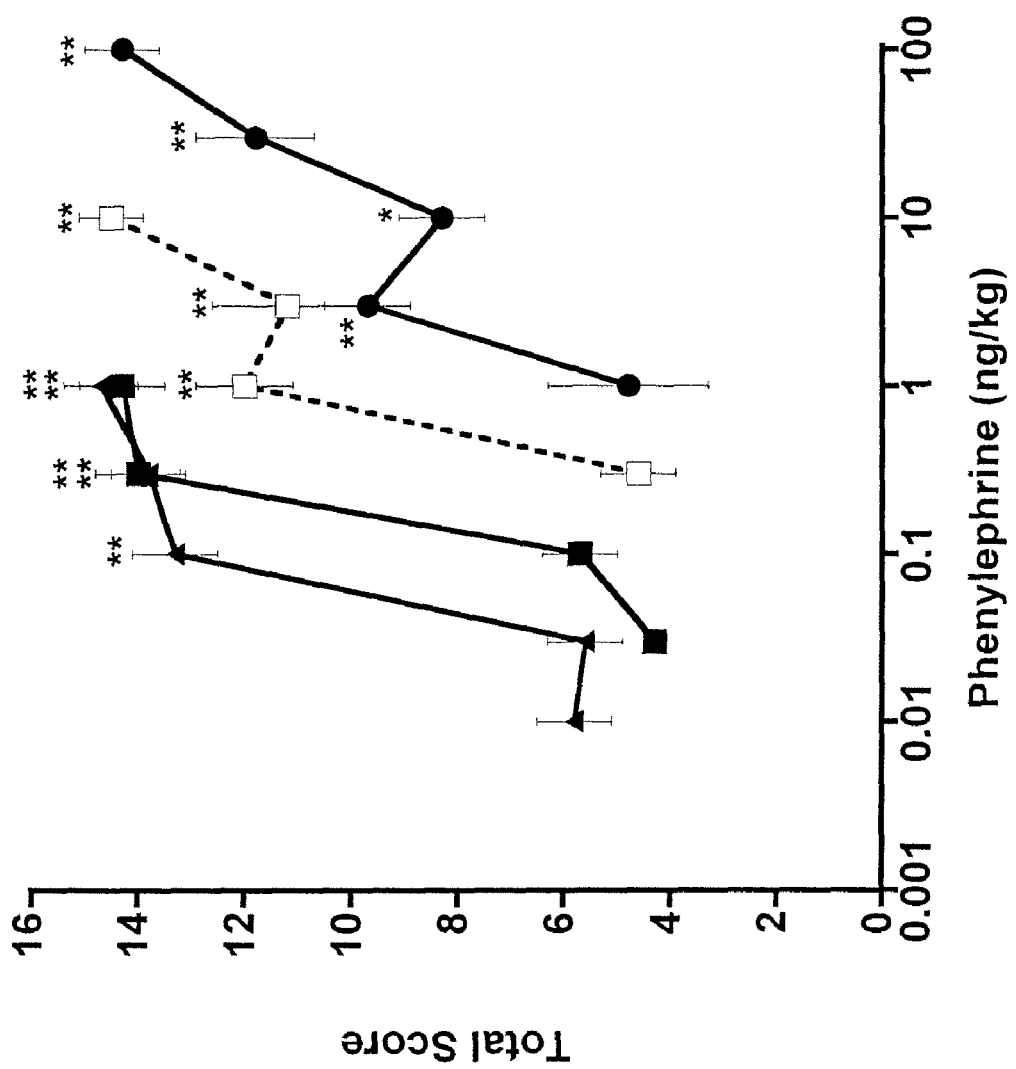
FIG. 2 shows that the increased sympathetic tone of α-2A and α-2C knockout mice enhances induction of tactile hypersensitivity by α-1 receptor activation. Wildtype (filled circle), α-2A knockout (filled square), and α-2C knockout (filled triangle) mice were-injected intraperitoneally with increasing doses of phenylephrine and assayed for tactile hypersensitivity. α-2A knockout mice were pretreated with 50 mg/kg i.p. guanethidine to cause a temporary chemical sympathectomy 24-30 hours prior to an i.p. injection with phenylephrine (open square). Each group of mice consisted of 5-6 animals. The mean sensitization score and SEM were calculated and compared to a vehicle control group using an unpaired two-tailed t-test (* $p<0.01$, ** $p<0.001$).

B. Increased Sympathetic Tone of α-2A and α-2C Knockout Mice Enhances their Sensitivity to Induction of Tactile Hypersensitivity by α-1 Receptor Activation To assess whether sympathetic tone can influence susceptibility to sensory sensitization, the sensitivity of α-2A and α-2C knockout mice to chemical induction of tactile hypersensitivity was compared to the sensitivity of wildtype mice. The α-2A and α-2C knockout mice did not exhibit baseline tactile hypersensitivity when compared to wildtype controls. First, the concentration of phenylephrine that elicits tactile hypersensitivity was compared in the knockout and wildtype mice. As shown in FIG. 2, there was a dramatic leftward shift in the phenylephrine dose response in both the α-2A and α-2C knockout mice. These results demonstrate that the ability of phenylephrine to cause tactile hypersensitivity was enhanced in both α-2 knockout mouse lines, with a greater enhancement in the α-2C knockout mice. In particular, compared with a strongly tactile hypersensitivity-inducing dose of 30 ng/kg phenylephrine in the wildtype line, 0.1 and 0.3 ng/kg phenylephrine resulted in maximal hypersensitivity in the α-2C and α-2A knockout mice, respectively. As further evidenced in FIG. 2, the gradual biphasic dose-response in the wildtype mice became a steeper dose-response in both lines of knockout mice.

Systemic administration of guanethidine results in a functional sympathectomy by depleting noradrenaline from sympathetic terminals. In order to test if shifts in the phenylephrine dose response curves were due to increased sympathetic tone in the α-2 knockout mice, α-2A knockout mice were chemically sympathectomized by guanethidine treatment (50 mg/kg i.p.) and assayed for phenylephrine-induced sensitivity 24-30 hours later. In guanethidine-treated α-2A mice, the increased sensitivity to phenylephrine was partly ablated so that the dose response was similar to the biphasic dose response observed in wildtype mice (see FIG. 2). These results confirm that increased sympathetic tone enhances sensory sensitization in α-2A knockout mice.

Figure 3:
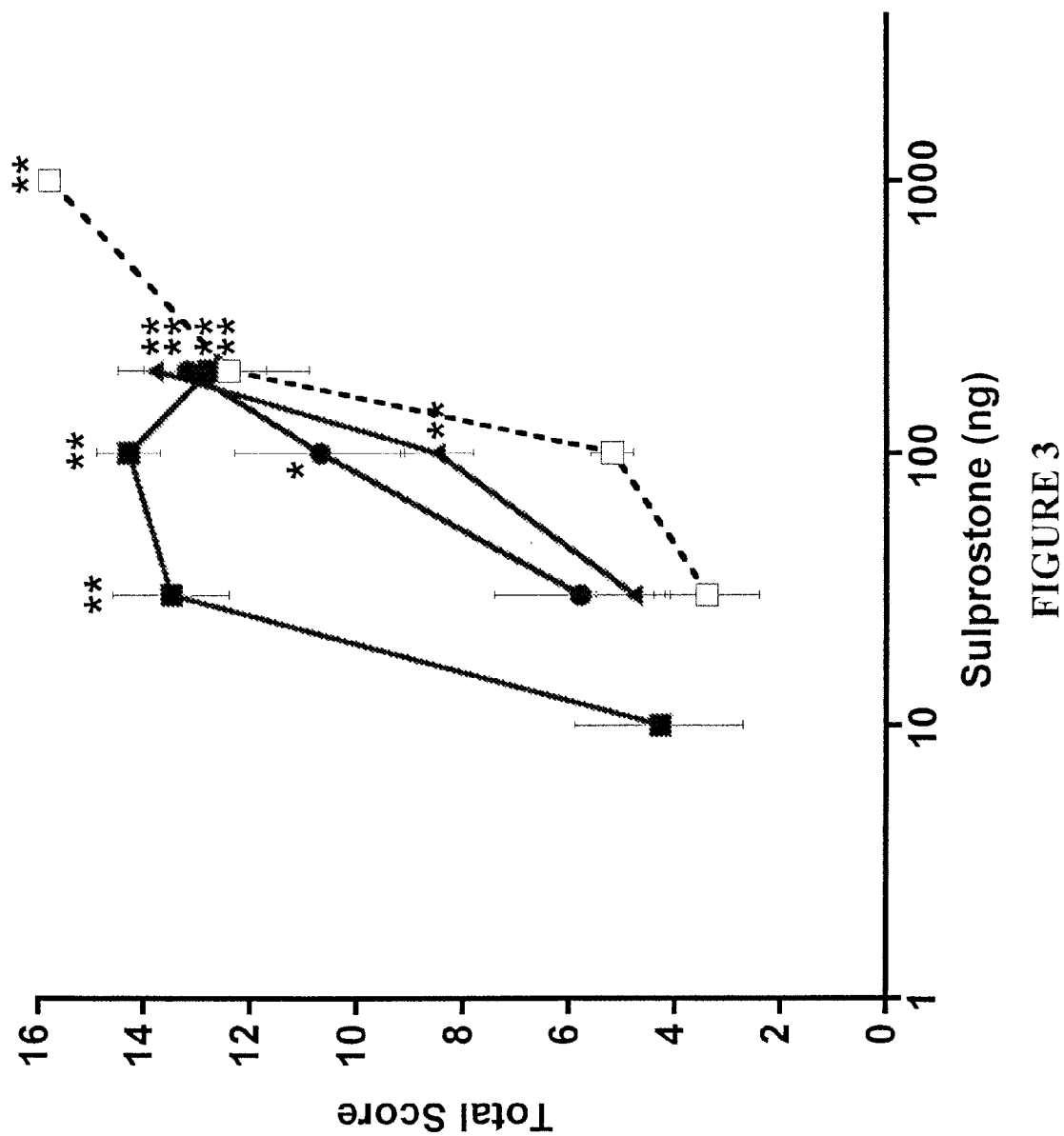
FIG. 3 shows that the sympathetic nervous system enhances sulprostone-induced tactile hypersensitivity. Wildtype (filled circle), α-2A (filled square), and α-2C (filled triangle) knockout mice were injected intrathecally with increasing doses of sulprostone and assayed for tactile hypersensitivity. α-2A knockout mice were pretreated with guanethidine (50 mg/kg i.p.) to cause a temporary chemical sympathectomy 24 hours prior to an intrathecal sulprostone injection (open square). Each group of mice consisted of 5-6 animals. The mean sensitization score and SEM were calculated and compared to a vehicle control group using an unpaired two-tailed t-test (* p<0.01, ** p<0.001).

C. The Sympathetic Nervous System Enhances Sulprostone-induced Tactile Hypersensitivity Sulprostone was injected intrathecally at increasing concentrations into wildtype and α-2 knockout mice in order to determine whether the knockout mice were more sensitive to sensitization of primary afferents. As shown in FIG. 3, the dose response of sulprostone was identical in the wildtype and α-2C knockout mice, but was shifted to the left in the α-2A knockout mice. In particular, a 30 ng dose was maximally effective in the α-2A knockout mice compared to a partially hypersensitivity-inducing dose of 100 ng and a maximal dose of 200 ng in the wild-type and α-2C knockout mice. A guanethidine (50 mg/kg i.p.) chemical sympathectomy decreased the sensitivity of the α-2A knockout mice to sulprostone. As shown in FIG. 3, the dose response of sulprostone-induced tactile hypersensitivity was shifted approximately 10-fold to the right in the α-2A knockout mice treated with guanethidine. These results demonstrate that the sympathetic nervous system enhances sulprostone sensitization.

Figure 4:
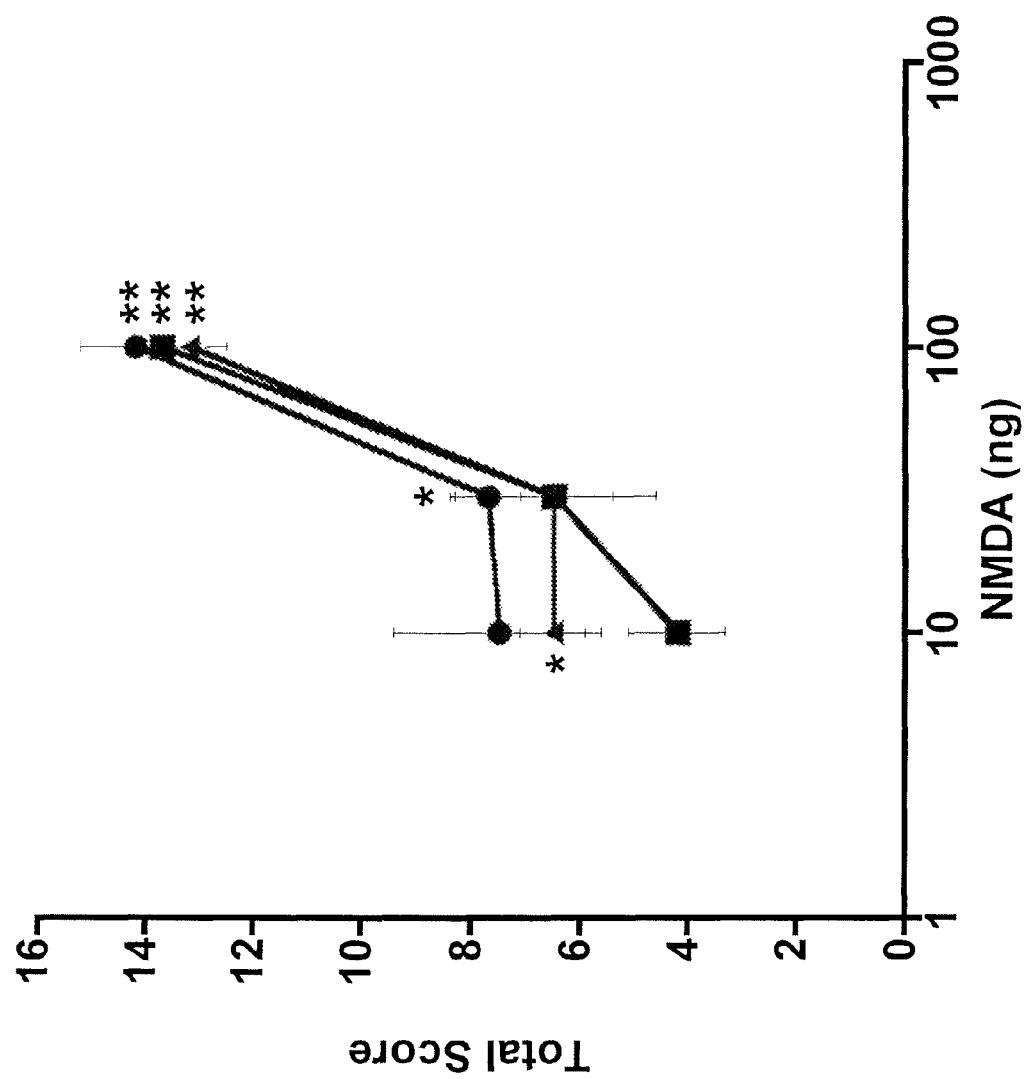
FIG. 4 shows that α-2 knockout mice do not exhibit altered NMDA-induced tactile hypersensitivity. Wildtype (filled circle), α-2A (filled square), and α-2C (filled triangle) knockout mice were injected intrathecally with increasing doses of NMDA. Each group of 5-6 mice was scored for tactile hypersensitivity. The mean response and SEM were calculated and compared to a vehicle control group using an unpaired two-tailed t-test (* p<0.01, ** p<0.001).

D. The Sympathetic Nervous System does not Contribute to NMDA-induced Tactile Hypersensitivity To assess whether α-2 knockout mice are more sensitive to dorsal horn sensitization by NMDA, wildtype and α-2 knockout mice were injected with varying concentrations of NMDA. As shown in FIG. 4, α-2A and α-2C knockout mice are not more sensitive to NMDA than wildtype mice. These results indicate that the sympathetic nervous system does not appear to contribute to NMDA-induced tactile hypersensitivity.

In sum, these results demonstrate that α-2 knockout mice exhibit elevated levels of sympathetic nerve activity and further indicate that these mice exhibit enhanced sensitization which is specific to the site and mode of stimulation.

EXAMPLE III

Comparison of Activity of α-2 Agonists Brimonidine and Clonidine

This example demonstrates that α-adrenergic agonists differ in their ability to alleviate sensory hypersensitivity that is enhanced by the sympathetic nervous system.

A. Brimonidine, But not Clonidine, Alleviates Sympathetically-enhanced Tactile Hypersensitivity Spinally administered α-2 adrenergic agonists alleviate neuropathic pain through a spinal α-2A receptor. To determine if the increased sympathetic activity in α-2 knockout mice alters the analgesic activity of the α-2 agonists, several agonists were assayed for activity. The α-2 agonists brimonidine and clonidine were first tested in the NMDA model in which sensitization is not influenced by the basal sympathetic tone of the knockout mice. Intrathecal co-administration of NMDA with either clonidine or brimonidine resulted in complete inhibition of tactile hypersensitivity in the wildtype and α-2C (FIGS. 5a and c, respectively) knockout mice. As expected, neither clonidine nor brimonidine inhibited NMDA-induced tactile hypersensitivity in the α-2A knockout mice (FIG. 5c), consistent with previous studies showing that a spinal α-2A adrenergic receptor subtype mediates analgesic actions of α-2 adrenergic agonists (Lakhlani et al., Proc. Natl. Acad. Sci. USA 94:9950-9955 (1997); Stone et al., J. Neurosci. 17:7157-1765 (1997); Hunter et al., Br. J. Pharmacol. 122:1339-1344 (1997)). The same pattern of analgesic activity of brimonidine also was observed in the sulprostone-induced tactile hypersensitivity model, which is sensitive to sympathetic tone (see FIGS. 5b and d). In contrast, the results obtained with clonidine were strikingly different: clonidine was analgesic in wildtype mice, but not in α-2A or α-2C knockout mice (compare FIGS. 5b and d). These results demonstrate that α-2 pan-agonists can have differential activity in sympathetically-enhanced conditions, with brimonidine exhibiting activity while clonidine is inactive.

B. Brimonidine, but not clonidine or tizanidine, Alleviates Sulprostone-induced Hypersensitivity in the Absence of Sedation Sedation limits the utility of many pharmaceuticals, including α-2 agonists. The α-2 agonists were therefore compared to test whether there was a difference in the dose that resulted in alleviation of sensory hypersensitivity relative to the dose that resulted in sedation.

For three α-2 agonists (tizanidine, clonidine and brimonidine), sedative effects and the ability to block tactile hypersensitivity were compared at various doses in models of locomotor activity and sulprostone-induced tactile hypersensitivity, respectively. The tactile hypersensitivity of 5-6 mice per group was scored every five minutes between 15 and 50 minutes following intraperitoneal dosing. Vehicle treated animals typically had a score of about 4. In addition, the locomotor activity of 5-6 mice per group was measured in a five minute period 30 minutes following intraperitoneal dosing. The locomotor activity relative to vehicle-treated animals was expressed as a percentage; percentage sedation was calculated as 100% minus the percent locomotor activity. As shown in FIG. 6, of the three α-adrenergic agonists assayed, only brimonidine produced an analgesic effect that was separable from sedation. These results demonstrate that brimonidine is distinct from other α-2 pan-agonists such as clonidine and tizanidine in the ability to alleviate sympathetically-enhanced disorders such as sulprostone-induced tactile hypersensitivity without concomitant sedation.

C. Variable α-2 Versus α-1 Functional Selectivity of α-Adrenergic Pan-agonists

The α-adrenergic receptor pharmacological profiles of brimonidine and clonidine were analyzed in assays using cell lines stably expressing α-2A, α-2C, α-1A and α-1B receptors.

Consistent with previous studies, the order of potency for inhibiting forskolin-induced cAMP accumulation in PC12 cells stably expressing either α-2A or α-2C receptor (FIGS. 7a, b; Table 2) was dexmedetomidine, which was greater than or equal to brimonidine, which was greater than clonidine, which was greater than tizanidine, which was greater than or equal to phenylephrine (Jasper et al., Biochem. Pharmacol. 55:1035-1043 (1998); Pihlavisto et al., Eur. J. Pharmacol. 385:247-253 (1999)). Brimonidine, clonidine and tizanidine were approximately 10-fold more potent at the α-2A receptor than the α-2C receptor.

The same compounds were functionally tested for the ability to stimulate α-1-mediated increases in intracellular calcium in HEK293 cells stably expressing the α-1A and α-1B receptor (FIGS. 7c, d; Table 2). The order of potency at the α-1A and α-1B receptors was phenylephrine, which was greater than clonidine, which was greater than tizanidine, which was equal to dexmedetomidine, which was greater than brimonidine. The α-2 agonists, clonidine, tizanidine and dexmedetomidine, were partial agonists while brimonidine exhibited weak activity at the α-1A receptor and no activity at the α-1B receptor. Thus, although clonidine and tizanidine have previously been characterized as "α-2 selective" agonists in binding assays, these compounds display a less than 10-fold selectivity between α-2 and α-1 receptor activation in functional assays. In contrast, dexmedetomidine was approximately 300-fold selective in functional assays, and brimonidine, the most highly selective compound in functional assays, exhibited greater than 1000-fold selectivity for α-2 receptors relative to α-1 receptors (see Table 2). These results demonstrate that brimonidine is a highly selective α-2 versus α-1 agonist and that the differential α-2/α-1 selectivity of brimonidine contrasts with the selectivity of other pan-agonists such as clonidine.

The difference in α-2/α-1 selectivity between clonidine and brimonidine indicates that the α-1 agonist activity of clonidine can augment the increased sympathetic tone of the α-2C knockout mice and mask the analgesic activity of clonidine in the sulprostone model. These results are supported by the ability of co-administration of the α-1 antagonist prazosin with clonidine to restore the analgesic activity of clonidine in α-2C knockout mice (FIG. 7e). Prazosin had no analgesic activity by itself in wildtype or α-2C knockout mice.

In sum, these results indicate that the loss of clonidine, but not brimonidine, analgesic activity in the α-2C knockout mice can be a result of clonidine's α-1 agonist activity and that the α-1 agonist activity of many "α-2 agonists" can limit their ability to treat stress-associated and other sympathetically-enhanced disorders.

Stable cell lines expressing an adrenergic receptor were established as follows. The bovine α-1A, hamster α-1B, human α-2A and human α-2C receptor cDNAs were blunt-end subcloned into the NheI-EcoRI sites in the retroviral vector pCL BABE Puro. The retroviral constructs were verified by double stranded DNA sequencing. High titer pseudotyped retroviral particles were produced by co-transfecting HEK293GP, a HEK293 cell line stably expressing Gag-Pol of the Maloney leukemia virus, with the appropriate retroviral vector and pMD.G, an expression vector for the vesicular stomatitis virus envelope protein, VSV-G. Sixteen hours after transfection, the media (DMEM, 10% FCS) was changed; the high titer (~1×10$^6$ pfu/mL) media was then harvested forty-eight hours later. The supernatant was filtered through a 0.4 uM filter.

The human α-2A and α-2C receptor supernatants were added, in varying amounts, to naive PC12 cells, which were then incubated for 48 hours. The transduced cell populations were replated at a lower density and grown in media containing 100 μg/ml puromycin. Non-transduced cells were killed within three days, and single foci grew within two months. The foci were picked, expanded, and assayed for receptor density by brimonidine radioligand binding. Functional α-2 receptor activity was confirmed by inhibition of forskolin-induced cAMP accumulation.

The bovine α-1A and hamster α-1B receptor supernatants were added, in varying amounts, to naive HEK293 cells, which were then incubated for 48 hours. The transduced cell populations were replated at a lower density and grown in media containing 0.25 ug/ml puromycin. Significant cell death was evident within three days, with single foci appearing within two weeks. After the foci were picked and expanded, expanded subclones were functionally assayed for α-1 receptor expression by measuring phenylephrine-induced intracellular $Ca^{+2}$ accumulation. Receptor density was measured in a prazosin radioligand binding assay.

Intracellular $Ca^{+2}$ responses were measured as follows in HEK293 cells stably expressing either the bovine α-1A or hamster α-1B adrenergic receptor. Between 40,000 to 50,000 cells were plated per well in 96-well poly-D-lysine coated plates in 0.2 ml DMEM containing 10% heat-inactivated fetal calf serum, 1% antibiotic-antimycotic and 0.25 μg/ml puromycin one day prior to use. Cells were washed twice with HBSS supplemented with 10 mM HEPES, 2.0 mM $CaCl_2$ and 2.5 mM probenecid, and subsequently incubated at 37° C. for 60 minutes with 4 μM Fluo-4 (Molecular Probes; Eugene, Oreg.). The extracellular dye was washed from the plates twice prior to placing the plates in the fluorometric imaging plate reader (FLIPR; Molecular Devices; Sunnyvale, Calif.). Ligands were diluted in HBSS and aliquoted into a 96-well microplate. Drugs were tested over the concentration range of 0.64 nM to 10,000 nM. Data for $Ca^{+2}$ responses were obtained in arbitrary fluorescence units.

Intracellular cAMP measurement was performed as follows. PC12 cells stably expressing the human α-2A or human α-2C adrenergic receptors were plated in 96-well poly-D-lysine coated plates at a density of 30,000 cells per well in 100 μl DMEM supplemented with 10% horse serum, 5% heat inactivated fetal bovine serum, 1% antibiotic-antimycotic and 100 μg/ml puromycin. Cells were grown overnight at 37° C. and 5% $CO_2$. Cells were dosed by adding an equal volume of media containing IBMX (to a final concentration of 1 mM), forskolin (to a final concentration of 10 μM) and the appropriate drug dilution (to a final concentration of between $10^{-5}$ M and $10^{-12}$ M). After a 10 minute incubation, the media was aspirated and the cells lysed with 200 μl lysis buffer (Amersham Biosciences; Piscataway, N.J.). Plates were stored at −20° C. for up to 24 hours prior to assay. Intracellular cAMP was determined using the Biotrak cAMP enzyme immunoassay system (Amersham Biosciences) according to the manufacturer's instructions. Plates were read on a plate reader at 450 nm.

Dose response curves for in vitro assays were generated using KaleidaGraph (Synergy Software; Reading, Pa.) by least squares fits to the equation, response=maximum response+((minimum response−maximum response)/(1+ (concentration of ligand/$EC_{50}$)). The percent efficacy was determined by comparing the maximum effect of the compound to the effect of a standard full agonist, which was phenylephrine for α-1 receptors and brimonidine for α-2 receptors.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

We claim:

1. A method of reducing the severity of a non-inflammatory dermatological condition in a subject, the method comprising topically administering to a subject in need of such reduction an effective amount of brimonidine or a pharmaceutically acceptable salt, ester, amide, sterioisomer or racemic mixture thereof.

TABLE 2

Functional α-2 versus α-1 selectivity of α-adrenergic agonists

| Compound | human $α_{2A}$ | | human $α_{2C}$ | | bovine $α_{1A}$ | | hamster $α_{1B}$ | | $α_{1A}/α_{2A}$ |
|---|---|---|---|---|---|---|---|---|---|
| | $EC_{50}$ | % E | $EC_{50}$ | % E | $EC_{50}$ | % E | $EC_{50}$ | % E | |
| Brimonidine | 0.86 ± 0.1 | 91 | 8 ± 3 | 93 | 1132 ± 281 | 15 | 943 ± 247 | 12 | 1316 |
| Dexmedetomidine | 0.8 ± .01 | 93 | 0.48 ± .2 | 90 | 376 ± 97 | 59 | 364 ± 72 | 62 | 289 |
| Clonidine | 10 ± 1 | 94 | 56 ± 28 | 84 | 89 ± 16 | 62 | 83 ± 10 | 63 | 8.9 |
| Tizanidine | 86 ± 35 | 93 | 1231 ± 376 | 85 | 264 ± 37 | 63 | 322 ± 31 | 61 | 3.1 |
| Phenylephrine | 306 ± 19 | 94 | 340 ± 131 | 87 | 9 ± 1 | 110 | 10 ± 1 | 110 | .03 |

The percent efficacy (% E) was determined by comparing the maximum effect of each agonist to the maximum effect of a standard full agonist (phenylephrine for α-1 receptors and brimonidine for α-2 receptors). The values represent the mean and SEM from 3-15 independent experiments. The fold-selectivity of the agonists for α-2 receptors relative to α-1 receptors was calculated from the ratio of their mean $EC_{50}$s for activating the α-1A and α-2A receptors.

* * * * *

UNITED STATES PATENT AND TRADEMARK OFFICE
CERTIFICATE OF CORRECTION

PATENT NO.         : 7,977,335 B2
APPLICATION NO.    : 12/114727
DATED              : July 12, 2011
INVENTOR(S)        : Daniel W. Gil et al.

Page 1 of 1

It is certified that error appears in the above-identified patent and that said Letters Patent is hereby corrected as shown below:

On the Cover page, item (56), under "Other Publications", in column 2, line 33, delete "Opthalmology," and insert -- Ophthalmology, --, therefor.

On the Cover page, item (56), under "Other Publications", in column 2, line 35, delete "Sustance" and insert -- Substance --, therefor.

On the Cover page, item (56), under "Other Publications", in column 2, line 36, delete "Intervies" and insert -- Interview --, therefor.

In column 3, line 47, delete "scare" and insert -- score --, therefor.

In column 3, line 56, delete "dexmeditomidine" and insert -- dexmedetomidine --, therefor.

In column 4, line 17, delete "+* p<0.001)." and insert -- ** p<0.001). --, therefor.

In column 4, line 43, delete "(α-2C" and insert -- α-2C --, therefor.

In column 4, line 47, delete "Artihano," and insert -- Artinano, --, therefor.

In column 7, line 7, delete "automatically." and insert -- automaticity. --, therefor.

In column 10, line 9, delete "photosensitivity" and insert -- phonosensitivity --, therefor.

In column 10, line 50, delete "opthalmoplegic" and insert -- ophthalmoplegic --, therefor.

In column 11, line 15, delete "a's" and insert -- as --, therefor.

In column 24, line 65, in claim 1, delete "sterioisomer" and insert -- stereoisomer --, therefor.

Signed and Sealed this
Thirteenth Day of September, 2011

David J. Kappos
*Director of the United States Patent and Trademark Office*